(12) United States Patent
Howarth et al.

(10) Patent No.: US 6,919,364 B2
(45) Date of Patent: *Jul. 19, 2005

(54) MICROBIOLOGICAL CONTROL IN ANIMAL PROCESSING

(75) Inventors: Jonathan N. Howarth, Baton Rouge, LA (US); James L. McNaughton, Quantico, MD (US)

(73) Assignee: Solution BioSciences, Inc., Salisbury, MD (US)

( * ) Notice: Subject to any disclaimer, the term of this patent is extended or adjusted under 35 U.S.C. 154(b) by 437 days.

This patent is subject to a terminal disclaimer.

(21) Appl. No.: 10/028,631

(22) Filed: Dec. 21, 2001

(65) Prior Publication Data

US 2003/0113402 A1 Jun. 19, 2003

Related U.S. Application Data

(63) Continuation-in-part of application No. 09/893,581, filed on Jun. 28, 2001, now abandoned.

(51) Int. Cl.$^7$ .............................................. A01N 43/50
(52) U.S. Cl. ...................... 514/389; 424/405; 424/406; 424/438; 424/442; 426/335; 119/231
(58) Field of Search ................................ 424/438, 442, 424/661, 662, 663, 665, 667, 673, 676, 709–711, 713, 723, 405, 406; 426/2, 335; 119/231, 72; 514/386, 389

(56) References Cited

U.S. PATENT DOCUMENTS

| | | | |
|---|---|---|---|
| 2,130,805 A | 9/1938 | Levine | |
| 2,392,505 A | 1/1946 | Rogers | |
| 2,398,598 A | 4/1946 | Rogers | |
| 2,779,764 A | 1/1957 | Paterson | |
| 2,795,556 A | 6/1957 | Quinn | |
| 2,888,787 A | 1/1959 | Paterson | |
| 2,920,997 A | 1/1960 | Wolf et al. | |
| 2,971,959 A | 2/1961 | Waugh et al. | |
| 2,971,960 A | 2/1961 | Waugh et al. | |
| 3,121,715 A | 2/1964 | Waugh et al. | |
| 3,147,219 A | 9/1964 | Paterson | |
| 3,147,259 A | 9/1964 | Paterson | |
| 3,152,073 A | 10/1964 | Morton ........................ | 210/62 |
| 3,170,883 A | 2/1965 | Owen et al. ................. | 252/187 |
| 3,308,062 A | 3/1967 | Gunther ...................... | 210/58 |
| 3,328,294 A | 6/1967 | Self et al. ..................... | 210/62 |
| 3,345,371 A | 10/1967 | Paterson | |
| 3,412,021 A | 11/1968 | Paterson | |
| 3,558,503 A | 1/1971 | Goodenough et al. ...... | 252/187 |
| 3,589,859 A | 6/1971 | Foroulis ........................ | 21/2.7 |
| 3,626,972 A | 12/1971 | Lorenzen | |
| 3,711,246 A | 1/1973 | Foroulis ........................ | 21/2.7 |
| 3,749,672 A | 7/1973 | Golton et al. ................ | 252/95 |
| 3,767,586 A | 10/1973 | Rutkiewic ............... | 252/187 H |
| 4,032,460 A | 6/1977 | Zilch et al. ............ | 252/8.55 B |
| 4,078,099 A | 3/1978 | Mazzola | |
| 4,119,535 A | 10/1978 | White et al. | |

(Continued)

FOREIGN PATENT DOCUMENTS

| | | |
|---|---|---|
| CA | 1230825 | 12/1987 |
| CA | 2042430 | 11/1991 |
| CA | 2163596 | 9/1996 |
| EP | 0106563 | 4/1984 |
| EP | 0177645 | 4/1986 |
| EP | 0228583 | 7/1987 |
| EP | 0177845 | 4/1988 |
| EP | 0206725 | 12/1988 |
| EP | 0550137 | 7/1993 |

(Continued)

OTHER PUBLICATIONS

Blaser, Martin J., et al., "Inactivation of *Campylobacter jejuni* by Chlorine and Monochloramine", Applied and Environmental Microbiology, vol. 51, No. 2, 1986, ppg 307–311.

Carr, Anitra C., "Differential reactivities of hypochlorous and hypobromous acids with pruified *Escherichia coli* phospholipid: formation of haloamines and halohydrins", Biochimica of Biophysica, 1392, 1998, ppg 254–264.

Dickens, J.A., et al., "Efficacy of an Herbal Extract on the Microbiological Quality of Broiler During a Simulated Chill", Poultry Science, 2000, vol. 79, ppg 1200–1203.

Fabrizio, K.A., et al., "Comparison of Electrolyzed Oxidizing Water with Various Antimicorbial Interventions to Reduce Salmonella Species on Poultry", Poultry Science, 2002, vol. 81, ppg 1598–1605.

OTHER PUBLICATIONS

Hawkins, Clare L., et al., "Hypochlorite– and Hypobromite– Mediated Radical Formation and Its Role in Cell Lysis", Archives of Biochemistry and Biophysics, vol. 395, No. 2, Nov. 15, 2001, ppg 137–145.

Kumar, Krishan, et al., "Kinetics and Mechanism of General–Acid–Assisted Oxidation of Bromide by Hypochlorite and Hypochlorus Acid", Inorg. Chem., 1987, vol. 26, ppg 2706–2711.

(Continued)

Primary Examiner—Neil S. Levy
(74) Attorney, Agent, or Firm—Sieberth & Patty, L.L.C.

(57) ABSTRACT

Fecal bacterial contamination in an animal is reduced by providing it with drinking water containing a microbiocidally-effective amount of halogen-based microbiocide resulting from mixing with water (A) a product formed in water from (i) bromine, chlorine, or bromine chloride, or any two or more thereof, (ii) a water-soluble source of sulfamate anion, and (iii) a water-soluble base; (B) at least one 1,3-dihalo-5,5-dialkylhydantoin in which one of the halogen atoms is a chlorine atom and the other is a chlorine or bromine atom, and in which each alkyl group, independently, contains in the range of 1 to about 4 carbon atoms; (C) at least one 1,3-dibromo-5,5-dialkylhydantoin in which one of the alkyl groups is a methyl group and the other alkyl group contains in the range of 1 to about 4 carbon atoms; or (D) any two or more of (A), (B), and (C).

24 Claims, No Drawings

U.S. PATENT DOCUMENTS

| | | |
|---|---|---|
| 4,126,717 A | 11/1978 | Mazzola |
| 4,136,052 A | 1/1979 | Mazzola |
| 4,199,001 A | 4/1980 | Kratz |
| 4,237,090 A | 12/1980 | DeMonbrun et al. ......... 422/13 |
| 4,242,216 A | 12/1980 | Daugherty et al. |
| 4,270,565 A | 6/1981 | King, Sr. |
| 4,293,425 A | 10/1981 | Price |
| 4,295,932 A | 10/1981 | Pocius ........................ 162/161 |
| 4,327,151 A | 4/1982 | Mazzola |
| 4,331,174 A | 5/1982 | King, Sr. |
| 4,382,799 A | 5/1983 | Davis et al. |
| 4,427,435 A | 1/1984 | Lorenz et al. ................. 71/67 |
| 4,427,692 A | 1/1984 | Girard |
| 4,451,376 A | 5/1984 | Sharp |
| 4,465,598 A | 8/1984 | Darlington et al. ......... 210/721 |
| 4,465,839 A | 8/1984 | Schulte et al. |
| 4,476,930 A | 10/1984 | Watanabe ................... 166/279 |
| 4,490,308 A | 12/1984 | Fong et al. ............. 260/513 N |
| 4,532,330 A | 7/1985 | Cole |
| 4,534,963 A | 8/1985 | Gordon |
| 4,537,697 A | 8/1985 | Girard |
| 4,539,071 A | 9/1985 | Clifford et al. ............. 162/161 |
| 4,546,156 A | 10/1985 | Fong et al. ................. 526/240 |
| 4,560,766 A | 12/1985 | Girard et al. |
| 4,566,973 A | 1/1986 | Masler, III et al. ......... 210/701 |
| 4,571,333 A | 2/1986 | Hsiao et al. |
| 4,595,517 A | 6/1986 | Abadi ........................ 252/82 |
| 4,595,691 A | 6/1986 | LaMarre et al. ............. 514/367 |
| 4,597,941 A | 7/1986 | Bottom et al. |
| 4,604,431 A | 8/1986 | Fong et al. ................. 525/351 |
| 4,621,096 A | 11/1986 | Cole |
| 4,642,194 A | 2/1987 | Johnson ...................... 210/699 |
| 4,643,835 A | 2/1987 | Koeplin-Gall et al. ...... 210/754 |
| 4,654,424 A | 3/1987 | Girard et al. |
| 4,659,359 A | 4/1987 | Lorenz et al. |
| 4,661,503 A | 4/1987 | Martin et al. ............... 514/372 |
| 4,662,387 A | 5/1987 | King, Sr. |
| 4,677,130 A | 6/1987 | Puzig |
| 4,680,339 A | 7/1987 | Fong ........................ 525/54.11 |
| 4,680,399 A | 7/1987 | Buchardt .................... 546/139 |
| 4,681,948 A | 7/1987 | Worley ........................ 548/319 |
| 4,692,335 A | 9/1987 | Iwanski |
| 4,698,165 A | 10/1987 | Theyson |
| 4,703,092 A | 10/1987 | Fong ........................ 525/351 |
| 4,711,724 A | 12/1987 | Johnson ...................... 210/699 |
| 4,713,079 A | 12/1987 | Chun et al. |
| 4,728,453 A | 3/1988 | Choy |
| 4,745,189 A | 5/1988 | Lee et al. |
| 4,752,443 A | 6/1988 | Hoots et al. ................... 422/13 |
| 4,759,852 A | 7/1988 | Trulear ...................... 210/699 |
| 4,762,894 A | 8/1988 | Fong et al. ................. 525/344 |
| 4,767,542 A | 8/1988 | Worley ........................ 210/755 |
| 4,770,884 A | 9/1988 | Hill et al. |
| 4,777,219 A | 10/1988 | Fong ........................ 525/329.4 |
| 4,780,197 A | 10/1988 | Schuman |
| 4,801,388 A | 1/1989 | Fong et al. ................. 210/701 |
| 4,802,990 A | 2/1989 | Inskeep, Jr. ................. 210/699 |
| 4,803,079 A | 2/1989 | Hsiao et al. |
| 4,822,512 A | 4/1989 | Auchincloss ................. 252/106 |
| 4,822,513 A | 4/1989 | Corby ........................ 252/106 |
| 4,846,979 A | 7/1989 | Hamilton .................... 210/754 |
| 4,867,895 A | 9/1989 | Choy |
| 4,883,600 A | 11/1989 | MacDonald et al. ........ 210/696 |
| 4,886,915 A | 12/1989 | Favstritsky ................. 564/503 |
| 4,898,686 A | 2/1990 | Johnson .................... 252/389.2 |
| 4,906,651 A | 3/1990 | Hsu ........................ 514/372 |
| 4,919,841 A | 4/1990 | Kamel et al. |
| 4,923,634 A | 5/1990 | Hoots et al. ............. 252/389.2 |
| 4,925,866 A | 5/1990 | Smith |
| 4,929,424 A | 5/1990 | Meier et al. ................... 422/9 |
| 4,929,425 A | 5/1990 | Hoots et al. ................... 422/13 |
| 4,964,892 A | 10/1990 | Hsu |
| 4,966,716 A | 10/1990 | Favstritsky et al. ......... 210/755 |
| 4,992,209 A | 2/1991 | Smyk et al. ................. 252/387 |
| 4,995,987 A | 2/1991 | Whitekettle et al. ........ 210/754 |
| 5,034,155 A | 7/1991 | Soeder et al. ........... 252/389.23 |
| 5,035,806 A | 7/1991 | Fong et al. ................. 210/701 |
| 5,047,164 A | 9/1991 | Corby ........................ 252/106 |
| 5,055,285 A | 10/1991 | Duncan et al. ............. 423/473 |
| 5,057,612 A | 10/1991 | Worley et al. ............. 548/301 |
| 5,076,315 A | 12/1991 | King |
| 5,118,426 A | 6/1992 | Duncan et al. ............. 210/721 |
| 5,120,452 A | 6/1992 | Ness et al. .................. 210/754 |
| 5,120,797 A | 6/1992 | Fong et al. ............. 525/329.4 |
| 5,137,563 A | 8/1992 | Valkanas |
| 5,141,652 A | 8/1992 | Moore, Jr. et al. .......... 210/754 |
| 5,179,173 A | 1/1993 | Fong et al. ............. 525/329.4 |
| 5,192,459 A | 3/1993 | Tell et al. .................. 252/106 |
| 5,194,238 A | 3/1993 | Duncan et al. ............. 423/473 |
| 5,196,126 A | 3/1993 | O'Dowd .................... 210/754 |
| 5,202,047 A | 4/1993 | Corby ........................ 252/106 |
| 5,208,057 A | 5/1993 | Greenley et al. ........... 426/332 |
| 5,218,983 A | 6/1993 | King |
| 5,259,985 A | 11/1993 | Nakanishi et al. .......... 252/180 |
| 5,264,136 A | 11/1993 | Howarth et al. ............ 210/754 |
| 5,264,229 A | 11/1993 | Manning et al. |
| 5,286,479 A | 2/1994 | Garlich et al. ................ 424/54 |
| 5,320,829 A | 6/1994 | Garlich et al. ................ 424/54 |
| 5,338,461 A | 8/1994 | Jones |
| 5,339,889 A | 8/1994 | Bigham |
| 5,384,102 A | 1/1995 | Ferguson et al. |
| 5,389,384 A | 2/1995 | Jooste ........................ 424/661 |
| 5,389,390 A | 2/1995 | Kross |
| 5,403,813 A | 4/1995 | Lichti et al. |
| 5,407,598 A | 4/1995 | Olson et al. ........... 252/186.35 |
| 5,409,711 A | 4/1995 | Mapelli et al. |
| 5,414,652 A | 5/1995 | Mieda et al. ................ 365/122 |
| 5,422,126 A | 6/1995 | Howarth et al. |
| 5,424,032 A | 6/1995 | Christensen et al. .......... 422/14 |
| 5,443,849 A | 8/1995 | Corby ........................ 424/667 |
| 5,460,833 A | 10/1995 | Andrews et al. |
| 5,464,636 A | 11/1995 | Hight et al. ................. 424/661 |
| 5,476,116 A | 12/1995 | Price et al. |
| 5,490,983 A | 2/1996 | Worley et al. ............. 424/405 |
| 5,490,992 A | 2/1996 | Andrews et al. |
| 5,525,241 A | 6/1996 | Clavin et al. ............... 210/753 |
| 5,527,547 A | 6/1996 | Hight et al. ................. 424/661 |
| 5,565,109 A | 10/1996 | Sweeny |
| 5,565,576 A | 10/1996 | Hall et al. |
| 5,578,559 A | 11/1996 | Dolan et al. |
| 5,589,106 A | 12/1996 | Shim et al. ................. 252/387 |
| 5,591,692 A | 1/1997 | Jones et al. |
| 5,603,941 A | 2/1997 | Farina et al. |
| 5,607,619 A | 3/1997 | Dadgar et al. ............ 252/187.2 |
| 5,610,126 A | 3/1997 | Barford et al. |
| 5,614,528 A | 3/1997 | Jones et al. |
| 5,622,708 A | 4/1997 | Richter et al. .............. 424/405 |
| 5,670,451 A | 9/1997 | Jones et al. |
| 5,670,646 A | 9/1997 | Worley et al. ........... 548/301.1 |
| 5,679,239 A | 10/1997 | Blum et al. ................. 205/536 |
| 5,683,654 A | 11/1997 | Dallmier et al. .............. 422/14 |
| 5,750,061 A | 5/1998 | Farina et al. |
| 5,753,602 A | 5/1998 | Hung et al. |
| 5,756,440 A | 5/1998 | Watanabe et al. |
| 5,763,376 A | 6/1998 | Ward et al. |
| 5,780,641 A | 7/1998 | Yerushalmi et al. |
| 5,795,487 A | 8/1998 | Dallmier et al. ............ 210/754 |
| 5,808,089 A | 9/1998 | Worley et al. ........... 548/318.5 |
| 5,830,511 A | 11/1998 | Mullerat et al. ............ 424/661 |
| 5,859,060 A | 1/1999 | Platt |
| 5,889,130 A | 3/1999 | Worley et al. ............. 526/261 |

| | | | |
|---|---|---|---|
| 5,891,499 A | 4/1999 | Balsano | |
| 5,900,512 A | 5/1999 | Elnagar et al. | 568/14 |
| 5,902,818 A | 5/1999 | Worley et al. | 514/376 |
| 5,922,745 A | 7/1999 | McCarthy et al. | 514/372 |
| 5,942,126 A | 8/1999 | Dallmier et al. | 210/756 |
| 5,942,153 A | 8/1999 | Heydel | |
| 5,958,853 A | 9/1999 | Watanabe | |
| 5,972,864 A | 10/1999 | Counts | |
| 5,981,461 A | 11/1999 | Counts et al. | |
| 5,984,994 A | 11/1999 | Hudson | |
| 6,004,587 A | 12/1999 | Mullerat et al. | 424/661 |
| 6,007,726 A | 12/1999 | Yang et al. | 210/752 |
| 6,007,735 A | 12/1999 | Creed | 252/186.25 |
| 6,015,782 A | 1/2000 | Petri et al. | 510/379 |
| 6,037,318 A | 3/2000 | Na et al. | 510/379 |
| 6,068,861 A | 5/2000 | Moore, Jr. et al. | 424/703 |
| 6,083,500 A | 7/2000 | Wooley et al. | 424/93.48 |
| 6,099,855 A | 8/2000 | Mullerat et al. | 424/442 |
| 6,110,387 A | 8/2000 | Choudhury et al. | 210/752 |
| 6,123,870 A | 9/2000 | Yang et al. | 252/186.1 |
| 6,156,229 A | 12/2000 | Yang et al. | 252/186.1 |
| 6,172,040 B1 | 1/2001 | Naidu | 514/6 |
| 6,270,722 B1 | 8/2001 | Yang et al. | 422/37 |
| 6,284,144 B1 | 9/2001 | Itzhak | |
| 6,287,473 B1 | 9/2001 | Yang et al. | 210/754 |
| 6,299,909 B1 | 10/2001 | Moore, Jr. et al. | 424/703 |
| 6,306,441 B1 | 10/2001 | Moore, Jr. et al. | 424/703 |
| 6,322,822 B1 | 11/2001 | Moore, Jr. et al. | 424/703 |
| 6,342,528 B1 | 1/2002 | McKenzie et al. | |
| 6,348,227 B1 | 2/2002 | Caracciolo, Jr. | |
| 6,448,410 B1 | 9/2002 | Howarth et al. | |
| 6,495,698 B1 | 12/2002 | Howarth | |
| 6,508,954 B1 | 1/2003 | Elnagar et al. | |
| 6,565,868 B1 | 5/2003 | Howarth et al. | |
| 6,605,253 B1 | 8/2003 | Perkins | |
| 6,605,308 B2 | 8/2003 | Shane et al. | |
| 6,638,959 B2 | 10/2003 | Howarth et al. | |
| 6,680,070 B1 | 1/2004 | Howarth et al. | |

FOREIGN PATENT DOCUMENTS

| | | |
|---|---|---|
| EP | 0581826 | 2/1994 |
| EP | 0584955 | 3/1994 |
| GB | 1054243 | 1/1967 |
| GB | 1139188 | 1/1969 |
| GB | 1600289 | 10/1981 |
| GB | 2267487 | 12/1993 |
| GB | 2273106 | 6/1994 |
| JP | 56158333 | 12/1981 |
| JP | 7299468 | 11/1995 |
| WO | WO 8802987 | 5/1988 |
| WO | WO 8910696 | 11/1989 |
| WO | 8910696 | 11/1989 |
| WO | 9015780 | 12/1990 |
| WO | WO 96/28173 | 9/1996 |
| WO | WO 9630491 | 10/1996 |
| WO | WO 9715652 | 5/1997 |
| WO | 9720546 | 6/1997 |
| WO | 9720909 | 6/1997 |
| WO | WO 9720909 | 6/1997 |
| WO | WO 9720548 | 8/1997 |
| WO | 9734827 | 9/1997 |
| WO | WO 9743264 | 11/1997 |
| WO | WO 9743392 | 11/1997 |
| WO | 9743392 | 11/1997 |
| WO | 9804143 | 2/1998 |
| WO | 9815609 | 4/1998 |
| WO | 9906320 | 2/1999 |
| WO | 9932596 | 7/1999 |
| WO | 9955627 | 11/1999 |
| WO | 0034186 | 6/2000 |
| WO | WO 0034188 | 6/2000 |
| WO | WO 01/52827 A1 | 7/2001 |
| WO | WO 0153209 | 7/2001 |

OTHER PUBLICATIONS

Lillard, H.S., "Effect of Trisodium Phosphate on Salmonellae Attached to Chicken Skin", Journal of Food Protection, vol. 57, No. 6, Jun. 1994, ppg 465–469.

Mead, G.C., et al., "The Effectiveness of In–plant Chlorination in Poultry Processing", Br. Poult. Sci., vol. 16, 1975, ppg 517–526.

Northcutt, J.K., et al., "Effect of Broiler Age, Feed Withdrawal, and Transportation on Levels of Coliforms, Campylobacter, *Escherichia coli* and Salmonella on Carcasses Before and After", Poultry Science, 2003, vol. 82,.

Patterson, J.T., "Chlorination of Water Used For Poultry Processing", British Poultry Science, vol. 9, part 2, 1968, ppg 129–133.

Selk, S.H. et al., "Comparative Antimicrobial Activity, In Vitro and In Vivo, of Soft N–Chloramine Systems and Chlorhexidine", Applied and Environmental Microbiology, Apr. 1982, pp 899–904.

Tamblyn, K.C., et al., "Utilization of the Skin Attachment Model to Determine the Antibacterial Efficacy of Potential Carcass Treatments", Poultry Science, 1997, vol. 76, ppg 1318–1323.

Tsai, Lee–Shin, et al., "Chlorination of Poultry Chiller Water: Chlorine Demand and Disinfection Efficiency", Poultry Science, 1992, vol. 71, ppg 188–196.

"Pathogen Reduction; Hazard Analysis and Critical Control Point (HACCP) Systems; Final Rule", Federal Register, Jul. 25 1996, vol 61, No 144, p. 38806–38814 and 38854–38855.

Vissers, Margret C.M., et al., "Comparison of human red cell lysis by hypochlorous and hypobromous acids: Insights into the mechanism of lysis", Biochem. J., vol. 330, 1998, ppg 131–138.

Vissers, Margret C.M., et al., "Fatty acid chlorohydrins and bromohydrins are cytotoxic to human endothelial cells", Redox Report, vol. 6, No. 1, 2001, ppg 49–55.

Wabeck, Charles J., "Methods to Reduce Microorganisms on Poultry", Broiler Industry, Dec. 1994, ppg 34, 36, 38, 40, 42.

Yang, Hong, et al., "Survival and Death of Salmonella Typhimurium and *Campylobacter jejuni* in Processing Water and on Chicken Skin during Poultry Scalding and Chilling", Journal of Food Protection, vol. 64, No. 6, 2001, ppg 770–.

"9215 C. Spread Plate Method", Microbiological Examintion (9000), ppg 9–38—9–40.

Corral et al., "Substitution in the Hydantoin Ring. III. Halogenation", J. Org. Chem., 1963, vol. 28, ppg. 1100–1104.

Jolles, "General Methods of Bromination", Bromine and its Compounds, 1966, Ernest Benn, London, ppg. 365.

Markish et al., "New Aspects on the Preparation of 1,3–Dibromo–5,5–Dimethydantoin", Ind. Eng. Chem. Res. 1995, vol. 34, ppg. 2125–2127.

Orazi et al., "Halogenacion con 3–Bromo–5,5–Dimetil–Hidantoina", Anales Assoc. Quim. Argentina, 1949, vol. 37, ppg. 192–196. (Not translated).

Orazi et al., "Halogenacion Con 1–3–Dibromo–5, 5–Dimetil–Hidantoina", Anales Assoc. Quim. Argentina, 1950, vol. 38, ppg. 5–11. (Not translated).

Gottardi: Reaction of Cl Br—In Aqueous solution (76 Zeutralks. Bakteriol., Parasiteukd,) In Fektionskr. Hgy., Abt. 1; Orig., Geihe B 162(3–4), ppg 384–388.
Mar., "Advanced Organic Chem.", 1992, $4^{th}$ Edition, ppg. 639–640.
HCAPLUS Abstract of JP 07171576 A2 issued 1995.
HCAPLUS Abstract of JP 07277912 A2 issued 1995.
HCAPLUS Abstract of JP 08027119 A2 issued 1996.
Chowhan et al., "Hardness Increase Induced by Partial Moisture Loss in Compressed Tablets and Its Effect on In Vitro Dissolution", J. Pharm. Sciences, Oct. 1978, vol. 67, No. 10, ppg. 1385–1389.
Krycer et al., "An Evaluation of Tablet Binding Agents Part II. Pressure Binders", Powder Technology, 1983, vol. 34, ppg. 53–56.
Petterson, "N–Halogen Compounds. I. Decomposition of 1,3–Dichloro–5,5–dimethylhydantoin in Water at pH 9", J. Org. Chem., 1959, vol. 24, ppg. 1414–1419.
HCAPLUS Abstract of JP 08239699 A2 issued 1996.
HCAPLUS Abstract of JP 09087684 A2 issued 1997.
HCAPLUS Abstract of JP 09227317 A2 issued 1997.
Hayward Pool Products Owner's Guide, Installation and Operatng Instructions, "Hayward Chemical Feeder", Models C250CF, C500CF, C1100CF, C1800CF, C2400CF, – 1998—4 pages.
Sani–King Spa Feeder Product Brochure Model 740 from King Technology Website, 2000, 4 pages.
Sani–King Adjust–A–Flo Product Brochure from King Technology Website 2000, 1 page.
Sani–King Perform–Max Sanitizers for Inground Pools Product Brochure for Model 940 & 960 from King Technology Website, 2000, 1 page.
Scrum—Fundamentals of General Chemistry, p. 315, 1955.
Al Zahrani, S.M., "Utilization of Polyethylene and Paraffin Waxes as Controlled Delivery Systems for Different Fertilizers", Ind. Eng. Chem. Res., 2000, vol 39, pp 369–371.
Frosti Abstract of Sundheim, G., et al., "Resistance of meat associated staphylococci to aquaternary ammonium compound", Food Microbiology, 1992, 9(2), 161–7. Accession No. 291734 Frosti.
Frosti Abstract of "Foodborne Pathogen Control", Poultry International, 1994, (Jul.), 62, author unknown. Accession No. 359896 Frosti.
Frosti Abstract of Smith, G., "Poultry industry looks to chlorine dioxide for pathogen control", Meat Processing, 1996, 35(10), 47. Accession No. 429057 Frosti.
Carpentier et al., "Biofimas and their consequences, with particular reference to hygiene in the food industry", Journal of Applied Bacteriology, 1993, vol. 75, ppg 499–511.
Mora et al., "Properties of a New Chloramine Disinfectant and Detoxicant", Poultry Science, 1982, vol. 61. ppg 1968–1971.
Mantilla–Sandholm et al., "Biofilm Formation in the Industry: A Review", Food Reviews International, 8(4), 1992, ppg 573–603.
Smith et al., "Potential Uses of Combined Halogen Disinfectants in Poultry Processing", Poultry Science, 1990, vol. 69, ppg 1590–1594.
Williams, et al., "Research Note: Combined Halogen Disinfectants in Poultry Processing", Poultry Science, 1990, vol. 69, ppg 2248–2251.
Worley, et al., "The Stabilities of New N–halamine Water Disinfectants", Wat. Res. vol. 21(8), ppg 983–988, 1987.

Willard et al., "Elementary Quantitative Analysis", Third Edition, Chapter XIV, 1933, ppg. 261–271.
Frosti Abstract of Bocharov D.A., "Disinfection of Poutry Processing Plant Objects", Proceedings of the $22^{nd}$ European meeting of Meat Research Workers, Malmo, Aug.:Sep., 1(C6), 4 pp. ., 1976. Accession No. 78674 Frosti.
CAPLUS Abstract of Heir, et al., "The Staphylococcus qacII gene product: a new member of the SMR family encoding multidrug resistance", FEMS 98 Microbiol. Lett. (1998), 163(1), ppg 49–56. Accession No. 1998:343309 CAPLUS.
Frosti Abstract of Lemaitre et al., "Plasmid–mediated resistance to antimicrobial agents among listeriae", Journal of Food Protection, 1998, Nov., 61(11),ppg 1459–1464. Accession No. 483547 Frost.
Frosti Abstract of Marriot, N.G., "Meat and poultry sanitation", Essentials of Food Sanitation, published by Chapman & Hall, London, 1997, 188–210. Accession No. 441637 Frosti.
Frosti Abstract of Mullerat et al., "Efficacy of Salmide, a sodium chlorite–based oxy–halogen disinfectant, to inactivate bacterial pathogens and extend shelf–life of broiler carcasses", Journal of Food Protection, 1994, 57(7), 596–603, Accession No. 353342 Frosti.
CAPLUS Abstract of Sanderson et al., "Case Reports: epidemic eye and upper respiratory irritation in poultry processing plants", Appl. Occup. Environ. Hyg, 1995, 10(1), 43–9. Accession No. 1995:439186 CAPLUS.
Frosti Abstract of Sheldon, B.W., "New and novel chemical and biological approaches for inhibiting pathogens and spoilage microorganisms associated with muscle food systems", Turkeys, 1996, 44(2), 9–12. Accession No. 410383 Frosti.
Ault et al., "Infrared and Raman Spectra of the $M+Cl_3$ ion Pairs and Their Chlorine–bromine Counterparts isolated in Argon Matrices", Journal of Chemical Physics, 1976, vol. 64, No. 12, ppg. 4853–4859.
CABA Copyright 2002 CABI Abstract of Bukh, K., "Use of Chlorine in Experiments on Controlling Swine Dysentary", Dansk Veterinaertidsskrift, (1988), vol. 71, No. 24, pp. 1278–1286. AN: 89:73404 CABA.
C.J. Nalepa, "New Bromine–Releasing Granules for Microbiological Control of Cooling Water," paper 03716 (Corrosion 2003 Houston, TX: NACE International, 2003), ppg 03716/1–03716/15.
Howarth, J.N., et al. "A New, Bromine–Releasing Solid for Microbiological Control of Cooling Water", IWC–01–05, (Pittsburgh, PA: Engineers' Society of Western Pennsylvania, 2001), ppg 1–7.
C.J. Nalepa, et al., "Strategies for Effective Control of Surface–Associated Microorganisms: A Literature Perspective," IWC–02–01 (Pittsburgh, PA: Engineers' Society of Western Pennsylvania, 2002), 19 pages.
C.J. Nalepa, et al., "The Control of Bacteria on Surfaces: Effectiveness of Bromine–Based Biocides towards Microbial Biofilms and Biofilm–Associated *Legionella pneumophia*," paper TP02–13 (Houston, TX; Cooling Technology Institute, 2002), 22 pages.
C.J. Nalepa, J.N. Howarth, and F.D. Azamia, "Factors to Consider When Applying Oxidizing Biocides in the Field, " paper 02223 (Houston, TX: NACE International, 2002), 20 pages.
C.J. Nalepa, "25 Years of Bromine Chemistry in Industrial Water Systems: A Review", Corrosion 2004, paper 04087 (Houston, TX, NACE International 2004), 30 pages.

MICROBIOLOGICAL CONTROL IN ANIMAL PROCESSING

REFERENCE TO RELATED APPLICATION

This is a continuation-in-part of application Ser. No. 09/893,581, filed Jun. 28, 2001 now abandoned.

REFERENCE TO OTHER APPLICATIONS

Reference is hereby made to the following applications: application Ser. No. 09/088,300, filed Jun. 1, 1998, now U.S. Pat. No. 6,068,861 issued May 30, 2000; application Ser. No. 09/296,499, filed Apr. 22, 1999, now U.S. Pat. No. 6,110,387 issued Aug. 29, 2000; application Ser. No. 09/323,348, filed Jun. 1, 1999, now U.S. Pat. No. 6,303,038 B1 issued Oct. 16, 2001; application Ser. No. 09/404,184, filed Sep. 24, 1999; application Ser. No. 09/442,025, filed Nov. 17, 1999, now U.S. Pat. No. 6,306,441 issued Oct. 23, 2001; application Ser. No. 09/451,319, filed Nov. 30, 1999; application Ser. No. 09/451,344, filed Nov. 30, 1999; application Ser. No. 09/456,781, filed Dec. 8, 1999; application Ser. No. 09/483,896, filed Jan. 18, 2000; application Ser. No. 09/484,687, filed Jan. 18, 2000; application Ser. No. 09/484,844, filed Jan. 18, 2000; application Ser. No. 09/484,891, filed Jan. 18, 2000; application Ser. No. 09/484,938, filed Jan. 18, 2000; application Ser. No. 09/487,816, filed Jan. 18, 2000; application Ser. No. 09/506,911, filed Feb. 18, 2000; application Ser. No. 09/658,839, filed Sep. 8, 2000; application Ser. No. 09/663,788, filed Sep. 18, 2000; application Ser. No. 09/663,948, filed Sep. 18, 2000, now U.S. Pat. No. 6,299,909 B1 issued Oct. 9, 2001; application Ser. No. 09/732,601, filed Dec. 7, 2000; application Ser. No. 09/775,516, filed Feb. 2, 2001; application Ser. No. 09/778,228, filed Feb. 6, 2001; application Ser. No. 09/785,890, filed Feb. 16, 2001; application Ser. No. 09/893,581, filed Jun. 28, 2001; application Ser. No. 09/974,622, filed Oct. 9, 2001; and application Ser. No. 10/029,329, filed Dec. 21, 2001 entitled "Microbiological Control in Poultry Processing" of which the owner is one of the two owners of the present application.

BACKGROUND

Animal processing for meat products is an area in which microbiological control is of vital importance. By the very nature of the processing involved there are numerous opportunities for the live animals to be exposed to various pathogens in the form of mobile bacteria. The thought of handling, processing and consuming bacteria-infested meat is revolting in the extreme. Furthermore, new government rules and standards require that additional attention be paid to both production and processing areas to assure reduced contamination of consumer meat.

Heretofore certain halogen-containing compositions have been proposed for use as additives to animal drinking water as a potential way of reducing bacterial activity. For example U.S. Pat. No. 4,822,512 describes tests in which a formulation composed of 1.5 parts of sodium chloride, 50 parts of potassium persulfate triple salt, 5 parts of sulfamic acid, 10 parts of malic acid, 18.5 parts of sodium hexametaphosphate and 15 parts of sodium dodecylbenzene was added to drinking water for poultry and day-old chicks. As to the results of these tests, the patent reports only that as compared to a control group the birds and chicks given this formulation gained more weight. In a paper published in *Poultry Science*, 1982, 61, 1968–1971, Mora, Kohl, Wheatley, Worley, Faison, Burkett, and Bodor report results of studies in which 15-day old broilers were given untreated drinking water or water treated with 200 ppm of 3-chloro-4,4-dimethyl-2-oxazolidinone (CDO). The authors concluded that during the 8-week period of the tests no significant differences were noted in the amounts of food or water consumed, that no statistically significant differences were seen between the weights of the test groups and their respective controls, and that no significant gross differences in internal organs were observed that could be attributed to the ingestion of the CDO. More recently, U.S. Pat. No. 6,099,855 teaches administration via drinking water to baby chicks and to 6-week-old male and female broilers infected with *Salmonella typhimurium* of pH-buffered redox-stabilized compositions comprising halide and oxyhalide ions. See also related U.S. Pat. Nos. 5,830,511; and 6,004,587. A product of this type, viz., Aquatize® biocide (Bioxy Incorporated) is believed to be a composition of this type.

One ubiquitous source of microbial contamination in animal processing is animal fecal matter. It would be of considerable benefit if a highly effective way could be found of reducing the bacterial content of animal fecal matter.

BRIEF SUMMARY OF THE INVENTION

This invention fulfills the foregoing need by providing and utilizing certain water-based compositions for reducing microbial contamination in and from animal fecal matter. Compositions of this invention have proven to be highly effective against fecal microbial contamination when used as drinking water for the animals. In addition, this invention makes possible the provision of microbiocidally-effective drinking water compositions for animals which result in little, if any, reduction in food and water consumption, and little, if any, adverse effect on intestinal condition of animals consuming such compositions. Moreover, microbiocidal agents used pursuant to this invention can be produced economically in straightforward processing from relatively low cost raw materials and because of their effectiveness when used as components of animal drinking water, can provide microbiological control on an economical basis consistent with the needs of the meat processing industry.

In one of its embodiments this invention provides a method of reducing fecal contamination in an animal, which method comprises providing to the animal drinking water containing a microbiocidally-effective amount of halogen-based microbiocide resulting from mixing with water:

A) a product formed in an aqueous medium from (i) bromine, chlorine, or bromine chloride, or any two or all three thereof, (ii) a water-soluble source of sulfamate anion, and (iii) a water-soluble base; or B) at least one 1,3-dihalo-5,5-dialkylhydantoin in which one of the halogen atoms is a chlorine atom and the other is a chlorine or bromine atom, and in which each of the alkyl groups, independently, contains in the range of 1 to about 4 carbon atoms; or C) at least one 1,3-dibromo-5,5-dialkylhydantoin in which one of the alkyl groups is a methyl group and the other alkyl group contains in the range of 1 to about 4 carbon atoms; or D) any two or more of A), B), and C) hereof.

This method is especially advantageous when used prior to slaughter (often termed as "preharvest") in the processing of animals for meat products. However the method is not limited to just preharvest. The method has other applications as well, such as reducing bacterial contamination in the soil, litter, or bedding that is found in animal rearing houses resulting from feces from domestic or farm animals, or improving the sanitation of facilities housing egg-laying hens.

Another embodiment of this invention is drinking water for animals, especially poultry, cattle, sheep, or swine, wherein said drinking water contains a microbiocidally-effective amount of halogen-based microbiocide resulting from mixing A), B), C), or D) above with water. In this connection, the term "animals" includes ruminants and monogastrics, such as domestic animals and pets, farm animals, animals raised for harvest, and so-called wild animals whether in zoos or in the wild. Such drinking water is useful in reducing the spread of diseases resulting from exposure to bacteria or other pathogens often contained in animal fecal matter. Such drinking water is preferably used in a facility for processing of animals for at least one meat product, such facility having at least one container of drinking water accessible to at least one animal prior to slaughter. The sanitation of the facility is improved and fecal bacterial contamination of the animals is reduced by the presence in such drinking water of a microbiocidally-effective amount of halogen-based microbiocide resulting from mixing A), B), C), or D) above with water.

A microbiocide from each of A), B), and C) has been shown to be effective against fecal bacteria when used in drinking water for such animals as poultry, cattle, and swine. Moreover, tests conducted under actual service conditions have indicated that at least 1,3-dibromo-5,5-dimethylhydantoin, N,N'-bromochloro-5,5-dimethylhydantoin, and an alkaline aqueous solution of product formed in an aqueous medium from bromine chloride and sodium sulfamate and sodium hydroxide did not create excessive mortality or weight gain loss in baby chicks prior to sacrifice.

In preferred embodiments, the halogen-based microbiocide added to the drinking water for the animals is (a) a bromine-based microbiocide comprising an overbased aqueous microbiocidal solution of one or more active bromine species, said species resulting from a reaction in water between bromine or bromine chloride, a mixture of bromine chloride and bromine, or a combination of bromine and chlorine in which the molar amount of chlorine is either equivalent to the molar amount of bromine or less than the molar amount of bromine, and a water-soluble source of sulfamate anion, or (b) at least one 1,3-dibromo-5,5-dialkylhydantoin in which one of the alkyl groups is a methyl group and the other alkyl group contains in the range of 1 to about 4 carbon atoms, or (c) both of (a) and (b) hereof. Such bromine-based microbiocides are more effective than corresponding chlorine-based microbiocides against various microorganisms. In addition, these bromine-based microbiocides tend to be less odorous than chlorine-based microbiocides, and are essentially devoid of unwanted bleaching activity. Moreover, while some of the bromine-based microbiocides may possibly react with nitrogenous species, such as are present in fecal matter, the resultant bromamines would also possess microbiological activity. Thus such side reactions would not materially decrease the microbiological effectiveness made available to the meat processor by use of these bromine-based microbiocides in the animal drinking water. Furthermore, bromamines generally do not exhibit obnoxious properties toward workers in the processing plant whereas chloramines resulting from use of certain chlorine-based microbiocides under the same conditions tend to be powerful lachrymators.

In particularly preferred embodiments, the halogen-based microbiocide added to the drinking water for the animals is at least one 1,3-dibromo-5,5-dialkylhydantoin in which one of the alkyl groups is a methyl group and the other alkyl group contains in the range of 1 to about 4 carbon atoms. Such bromine-based microbiocides are especially effective against fecal bacteria when used in the practice of this invention. 1,3-Dibromo-5,5-dimethylhydantoin is particularly preferred for use in the practice of this invention.

The aqueous microbiocidal solutions used as animal drinking water pursuant to this invention can be formed from microbiocides of types B) and/or C) above by mixing such microbiocidal agent(s) in undiluted form (i.e., in solid form such as powder, particles, granules, tablets, etc.) or as a preformed aqueous solution thereof with water to be used as drinking water for the animals. To form the finished suitably dilute animal drinking water solution of this invention the solids can thus be added to, mixed with, or dissolved in water in proportions such that the desired microbiocidally effective amount of one or more halogen species is present in the water as the result of a single step operation where the intended end use dosage level is achieved without further dilution. Alternatively the solids can be added to, mixed with, or otherwise introduced into water using proportions that result in a more concentrated solution (or slurry) which then is diluted with water one or more times to form a final solution in which the desired microbiocidally effective amount of one or more halogen species is present in the water. In all such cases, the resultant suitably dilute microbiocidal solution of this invention containing the appropriate microbiocidally effective amount of one or more halogen species the can then be used as animal drinking water to reduce fecal microbial contamination. The microbiocides of type A) above are typically prepared or provided in the form of a preformed aqueous concentrate containing, say, at least about 50,000 ppm (wt/wt) and preferably at least about 100,000 ppm (wt/wt) of active bromine and thus the concentrate is added to and mixed with, or diluted in stages, whichever is desired, to form the suitably dilute microbiocidal solution of this invention for use as animal drinking water. Such concentrates typically have an atom ratio of nitrogen from sulfamate to active bromine that is greater than about 0.93, and preferably greater than 1, and has a pH of at least about 12 and preferably in the range of about 13 to about 14. An aqueous concentrate of type A) is available in the marketplace as Stabrom® 909 biocide (Albemarle Corporation). Such commercially-available concentrates will typically contain in the range of about 145,000 to about 160,000 ppm of active bromine.

Other embodiments, features and advantages of this invention will be still further apparent from the ensuing description and appended claims.

FURTHER DETAILED DESCRIPTION OF THE INVENTION

One group of halogen-based microbiocides for use in this invention is an aqueous microbiocidal solution of one or more active halogen species, said species resulting from a reaction in water between bromine, chlorine, or bromine chloride, or any two or all three thereof, and a water-soluble source of sulfamate anion. If sulfamic acid is used in forming this microbiocide, the solution should also be provided with a base, preferably enough base to keep the solution alkaline, i.e., with a pH above 7, preferably above about 10 and most preferably about 13 or above. The lower the pH, the more unstable the solution, and thus if the solution is prepared on site for immediate use, the use of a base is not essential. However, it is preferable to employ a concentrated microbiocidal solution manufactured elsewhere, and in such case the concentrated solution would be provided as an overbased solution with a pH of, say, about 13 or more. Often such concentrated solutions will contain over 50,000 ppm (wt/wt) of active halogen, preferably at least about 100,000 ppm (wt/wt) of active halogen. Active halogen content is determinable by use of conventional starch-iodine titration. For convenience, products of this type are sometimes referred to hereinafter as sulfamate-stabilized bromine chloride or more simply, SSBC.

One preferred group of this type is a bromine-based microbiocidal solution formed by reacting bromine or, more preferably bromine chloride, a mixture of bromine chloride and bromine, or a combination of bromine and chlorine in which the molar amount of chlorine is either equivalent to the molar amount of bromine or less than the molar amount of bromine, in an aqueous medium with sulfamic acid and/or a water-soluble salt of sulfamic acid. Except when made on site for immediate use, such solutions should be highly alkaline solutions typically with a pH of at least about 12 and preferably at least about 13, such pH resulting from use of a base such as sodium hydroxide or the like, in producing the solution. The solution typically contains at least 100,000 ppm (wt/wt) of active bromine, e.g. as much as 145,000 to 160,000 ppm of active bromine. Processes for producing concentrated aqueous microbiocidal solutions of this type are described in U.S. Pat. No. 6,068,861, issued May 30, 2000, and U.S. Pat. No. 6,299,909 B1, issued Oct. 9, 2001, all disclosures of which are incorporated herein by reference. Concentrated solutions of this type are available in the marketplace, for example, Stabrom® 909 biocide (Albemarle Corporation).

It will be appreciated that even where the microbiocide is made from bromine chloride, a mixture of bromine chloride and bromine, or a combination of bromine and chlorine in which the molar amount of chlorine is either equivalent to the molar amount of bromine or less than the molar amount of bromine is used, the microbiocide is bromine-based as most of the chlorine usually winds up as a chloride salt such as sodium chloride since an alkali metal base such as sodium hydroxide is typically used in the processing to raise the pH of the product solution to at least about 13. Thus the chlorine in the product solution is not present as a significant microbiocide.

Another group of halogen-based microbiocides for use in this invention is one or more N,N'-dihalo-5,5-dialkyl hydantoins in which one of the halogen atoms is chlorine and the other is bromine or chlorine, and in which the alkyl groups, independently, each contain from 1 to about 4 carbon atoms. Suitable compounds of this type include, for example, such compounds as 1,3-dichloro-5,5-dimethylhydantoin, 1,3-dichloro-5,5-diethylhydantoin, 1,3-dichloro-5,5-di-n-butylhydantoin, 1,3-dichloro-5-ethyl-5-methylhydantoin, N,N'-bromochloro-5,5-dimethylhydantoin, N,N'-bromochloro-5-ethyl-5-methylhydantoin, N,N'-bromochloro-5-propyl-5-methylhydantoin, N,N'-bromochloro-5-isopropyl-5-methylhydantoin, N,N'-bromochloro-5-butyl-5-methylhydantoin, N,N'-bromochloro-5-isobutyl-5-methylhydantoin, N,N'-bromochloro-5-sec-butyl-5-methylhydantoin, N,N'-bromochloro-5-tert-butyl-5-methylhydantoin, N,N'-bromochloro-5,5-diethylhydantoin, and mixtures of any two or more of the foregoing. A mixture of 1,3-dichloro-5,5-dimethylhydantoin and 1,3-dichloro-5,5-diethylhydantoin is available under the trade designation Dantochlor® biocide (Lonza Corporation). N,N'-bromochloro-5,5-dimethylhydantoin is available commercially under the trade designation Bromicide® biocide (Great Lakes Chemical Corporation). Another suitable bromochlorohydantoin is composed of a mixture of a predominate amount by weight of N,N'-bromochloro-5,5-dimethylhydantoin together with a minor proportion by weight of 1,3-dichloro-5,5-dimethylhydantoin and 1,3-dichloro-5-ethyl-5-methylhydantoin. A mixture of this latter type is available in the marketplace under the trade designation Dantobrom® biocide (Lonza Corporation) which is believed to contain about 60 wt % of N,N'-bromochloro-5,5-dimethylhydantoin, about 27.4 wt % of 1,3-dichloro-5,5-dimethylhydantoin, about 10.6 wt % of 1,3-dichloro-5-ethyl-5-methylhydantoin, and about 2 wt % of inerts. As between the 1,3-dichloro-5,5-dialkylhydantoins and N,N'-bromochloro-5,5-dialkylhydantoins, the latter are preferred as they have greater microbiocidal effectiveness.

When a mixture of two or more of the foregoing N,N'-dihalo-5,5-dialkylhydantoin biocides is used pursuant to this invention, the individual biocides of the mixture can be in any proportions relative to each other.

It will be understood that the designation N,N' in reference to, say, N,N'-bromochloro-5,5-dimethylhydantoin means that this compound can be (1) 1-bromo-3-chloro-5,5-dimethylhydantoin, or (2) 1-chloro-3-bromo-5,5-dimethylhydantoin, or (3) a mixture of 1-bromo-3-chloro-5,5-dimethylhydantoin and 1-chloro-3-bromo-5,5-dimethylhydantoin. Also, it is conceivable that some 1,3-dichloro-5,5-dimethylhydantoin and 1,3-dibromo-5,5-dimethylhydantoin could be present in admixture with (1), (2), or (3).

An even more preferred system for use in the practice of this invention is a bromine-based microbiocidal solution of a 1,3-dibromo-5,5-dialkylhydantoin in which one of the alkyl groups is a methyl group and the other alkyl group contains in the range of 1 to about 4 carbon atoms. Thus these preferred biocides comprise 1,3-dibromo-5,5-dimethylhydantoin, 1,3-dibromo-5-ethyl-5-methylhydantoin, 1,3-dibromo-5-n-propyl-5-methylhydantoin, 1,3-dibromo-5-isopropyl-5-methylhydantoin, 1,3-dibromo-5-n-butyl-5-methylhydantoin, 1,3-dibromo-5-isobutyl-5-methylhydantoin, 1,3-dibromo-5-sec-butyl-5-methylhydantoin, 1,3-dibromo-5-tert-butyl-5-methylhydantoin, and mixtures of any two or more of them. Of these biocidal agents, 1,3-dibromo-5-isobutyl-5-methylhydantoin, 1,3-dibromo-5-n-propyl-5-methylhydantoin, and 1,3-dibromo-5-ethyl-5-methylhydantoin are, respectively, preferred, more preferred, and even more preferred members of this group from the cost effectiveness standpoint. Of the mixtures of the foregoing biocides that can be used pursuant to this invention, it is preferred to use 1,3-dibromo-5,5-dimethylhydantoin as one of the components, with a mixture of 1,3-dibromo-5,5-dimethylhydantoin and 1,3-dibromo-5-ethyl-5-methylhydantoin being particularly preferred. The most preferred member of this group of microbiocides is 1,3-dibromo-5,5-dimethylhydantoin. This compound is available in the marketplace in tablet or granular form under the trade designation Albrom® 100 biocide (Albemarle Corporation). Preferred is 1,3-dibromo-5,5-dimethylhydantoin in granular form with a compression strength of at least 15 pounds per inch and more preferably at least 20 pounds per inch, which is devoid of any binder or other additive component that tends to increase the compression strength of the granules, and which has not been melted to form the granules.

To determine the compression strength of granules, individual granules are subjected to crush strength testing utilizing a Sintech® 1/S compression apparatus (MTS Systems Corporation, Edenprairie, Minn.) equipped with Testworks software, which software is installed in the 1/S compression apparatus as supplied by MTS Systems Corporation. The apparatus includes a horizontal circular-shaped load cell interfaced with a computer, a digital micrometer also interfaced with the computer, and a vertical screw-driven piston that is disposed above the load cell and adapted to apply a downward force perpendicular to the load cell. The procedure for measuring crush strength involves measuring the thickness of the granule with the micrometer to provide a digitized input to the computer. Next the granule is placed on the load cell with the piston in contact with the upper surface of the granule. Then the apparatus is activated whereby the piston commences applying a progressively increasing downward force to the granule. At the same time, the load cell continuously measures the downward force being applied to the granule, and the input of such measurements is transmitted to the computer. When the force being applied reaches the point where the amount of force suddenly decreases to 10% of the immediately preceding force, the granule has reached the breaking point, and the application of the force is immediately terminated by the software program. From the inputs to the computer, two values are provided, namely the pounds of force at the breaking point of the granule, and the pounds of force per inch thickness of the granule at the breaking point. Thus the greater the force applied, the greater the strength. Typically, the test is conducted thirteen times using thirteen randomly selected granules. The results are then averaged.

When a mixture of two or more of the foregoing 1,3-dibromo-5,5-dialkylhydantoin biocides is used pursuant to this invention, the individual biocides of the mixture can be in any proportions relative to each other.

The halogen-based microbiocides used pursuant to this invention are typically employed in drinking water at dosage levels in the range of about 0.5 to about 25 ppm (wt/wt) expressed as $Cl_2$ equivalent. However whenever deemed necessary or appropriate, departures from this range are permissible and are within the scope of this invention.

Methods for producing 1,3-dibromo-5,5-dialkylhydantoins are known and reported in the literature.

The amount (concentration) of the selected microbiocide utilized in the practice of this invention may vary depending on various factors such as the particular microbiocide being used, the species, age and size of the animal(s) to which the drinking water is to be provided, the duration of the time during which the treated drinking water is to furnished to the animal(s), the nature and frequency of prior microbiocidal treatments, if any, to which the animal has been subjected, the types and nature of the microorganisms to which the animal has been exposed, and so on. In any event, a microbiocidally-effective amount of the microbiocide of this invention will be introduced into the water to be supplied to the animal(s) being treated. such that the amount of microbes or bacteria in the fecal matter of the animal is reduced. Yet the amount of such microbiocide should not be such as to (i) inhibit the animals from ingesting the treated water or (ii) leave excessive residues from the microbiocide in the edible portions of the animals. Optimal amounts of the microbiocide in the drinking water can be determined by performing preliminary tests with the particular microbiocide and type of animal being processed, using as a general guideline a microbiocidally-effective amount of active halogen in the range of about 1 to about 100 ppm (wt/wt), preferably in the range of about 4 to about 50 ppm (wt/wt), and more preferably in the range of about 4 to about 30 ppm (wt/wt) of active bromine. If the actual active halogen present is chlorine, these values are divided by 2.25. Thus the animal drinking water compositions of this invention for use with fowl, cattle, sheep, or swine will typically contain microbiocidally-effective amounts of active halogen in these ranges. In these concentration ranges, active chlorine or bromine content can be determined analytically by use of the conventional DPD test procedure. In the case of the 1,3-dibromo-5,5-dialkylhydantoins used pursuant to this invention, in ordinary situations concentrations will typically be within the range of about 1 to about 50 ppm (wt/wt) (i.e., about 0.5 to about 25 ppm wt/wt expressed as chlorine equivalent. Preferably the concentration of the 1,3-dibromo-5,5-dialkylhydantoin(s) in the water will be in the range of about 4 to about 20 ppm wt/wt, and more preferably in the range of about 5 to about 10 ppm of the 1,3-dibromo-5,5-dialkylhydantoin(s) in the water. It will be understood that departures from the foregoing ranges can be made whenever deemed necessary or desirable, and such departures are within the spirit and scope of this invention.

As can be seen from the above, there are two different types of analytical procedures that are used for determining active halogen content, whether active chlorine, active bromine or both. In the case of the more highly-soluble microbiocides used pursuant to this invention, to measure concentrations in the vicinity of above about, say, 2475 ppm (wt/wt) of active bromine or, say, above about 1100 ppm of active chlorine, starch-iodine titration is the preferred procedure. In the case of the less soluble microbiocides used pursuant to this invention, (i.e., the dibromodialkylhydantoins) to measure concentrations in the vicinity of above about, say, 1300 ppm (wt/wt) of active bromine or, say, above about 580 ppm of active chlorine, starch-iodine titration is the preferred procedure. On the other hand, where concentrations are below levels in the foregoing vicinities, the conventional DPD test procedure is more suitable, as this test is designed for measuring very low active halogen concentrations, e.g., active chlorine concentrations in the range of from zero to about 11–12 ppm (wt/wt) or active bromine concentrations in the range of from zero to about 25–27 ppm (wt/wt). In fact, where the actual concentration of active chlorine is between, say, about 11–12 ppm and about 1100 ppm (wt/wt), or the where the actual concentration of active bromine is between, say, about 25 ppm and about 2475 ppm (wt/wt), the test sample is typically diluted with pure water to reduce the actual concentration to be in the range of about 4 to about 11–12 ppm in the case of active chlorine and to be in the range of about 4.5 to about 12 ppm in the case of active bromine before making the DPD analysis. It can be seen therefore that while there is no critical hard-and-fast concentration dividing line between which procedure to use, the approximate values given above represent a practical approximate dividing line, since the amounts of water dilution of more concentrated solutions when using the DPD test procedure increase with increasing initial active halogen concentration, and such large dilutions can readily be avoided by use of starch-iodine titration when analyzing the more concentrated solutions. In short, with suitably dilute solutions use of the DPD test procedure is recommended, and with more concentrated solutions use of starch-iodine titration is recommended.

The starch-iodine titration procedure for determination of active halogen has long been known. For example, chapter XIV of Willard-Furman, *Elementary Quantitative Analysis*, Third Edition, D. Van Nostrand Company, Inc., New York, Copyright 1933, 1935, 1940 provides a description of starch-iodine titration. While details of standard quantitative analytical procedures for determination of active halogen in such product solutions by starch-iodine titration may vary from case to case, the results are normally sufficiently uniform from one standard procedure to another as not to raise any question of unreliability of the results. A recommended starch-iodine titration procedure is as follows: A magnetic stirrer and 50 milliliters of glacial acetic acid are placed in an iodine flask. The sample (usually about 0.2–0.5 g) for which the active halogen is to be determined is weighed and added to the flask containing the acetic acid. Water (50 milliliters) and aqueous potassium iodide (15%, wt/wt; 25 milliliters) are then added to the flask. The flask is stoppered using a water seal. The solution is then stirred for fifteen minutes, after which the flask is unstoppered and the stopper and seal area are rinsed into the flask with water. An automatic buret (Metrohm Limited) is filled with 0.1 normal sodium thiosulfate. The solution in the iodine flask is titrated with the 0.1 normal sodium thiosulfate; when a faint yellow color is observed, one milliliter of a 1 wt % starch solution in water is added, changing the color of the solution in the flask from faint yellow to blue. Titration with sodium thiosulfate continues until the blue color disappears. The amount of active halogen is calculated using the weight of the sample and the volume of sodium thiosulfate solution titrated. In this way, the amount of active halogen such as active chlorine or active bromine in an aqueous product solution, regardless of actual chemical form, can be quantitatively determined.

The standard DPD test for determination of low levels of active halogen is based on classical test procedures devised by Palin in 1974. See A. T. Palin, "Analytical Control of Water Disinfection With Special Reference to Differential DPD Methods For Chlorine, Chlorine Dioxide, Bromine, Iodine and Ozone", *J. Inst. Water Eng.*, 1974, 28, 139. While there are various modernized versions of the Palin procedures, the recommended version of the test is fully described in *Hach Water Analysis Handbook*, 3rd edition, copyright 1997. The procedure for "total chlorine" (i.e., active chlorine) is identified in that publication as Method 8167 appearing on page 379, Briefly, the "total chlorine" test involves introducing to the dilute water sample containing active halogen, a powder comprising DPD indicator powder, (i.e., N,N'-diethyldiphenylenediamine), KI, and a buffer. The active halogen species present react(s) with KI to yield iodine species which turn the DPD indicator to red/pink. The intensity of the coloration depends upon the concentration of "total chlorine" species (i.e., active chlorine") present in the sample. This intensity is measured by a colorimeter calibrated to transform the intensity reading into a "total chlorine" value in terms of mg/L $Cl_2$. If the active halogen present is active bromine, the result in terms of mg/L $Cl_2$ is multiplied by 2.25 to express the result in terms of mg/L $Br_2$ of active bromine.

In greater detail, the DPD test procedure is as follows:
1. To determine the amount of species present in the water which respond to the "total chlorine" test, the water sample should be analyzed within a few minutes of being taken, and preferably immediately upon being taken.
2. Hach Method 8167 for testing the amount of species present in the water sample which respond to the "total chlorine" test involves use of the Hach Model DR 2010 calorimeter. The stored program number for chlorine determinations is recalled by keying in "80" on the keyboard, followed by setting the absorbance wavelength to 530 nm by rotating the dial on the side of the instrument. Two identical sample cells are filled to the 10 mL mark with the water under investigation. One of the cells is arbitrarily chosen to be the blank. To the second cell, the contents of a DPD Total Chlorine Powder Pillow are added. This is shaken for 10–20 seconds to mix, as the development of a pink-red color indicates the presence of species in the water which respond positively to the DPD "total chlorine" test reagent. On the keypad, the SHIFT TIMER keys are depressed to commence a three minute reaction time. After three minutes the instrument beeps to signal the reaction is complete. Using the 10 mL cell riser, the blank sample cell is admitted to the sample compartment of the Hach Model DR 2010, and the shield is closed to prevent stray light effects. Then the ZERO key is depressed. After a few seconds, the display registers 0.00 mg/L $Cl_2$. Then, the blank sample cell used to zero the instrument is removed from the cell compartment of the Hach Model DR 2010 and replaced with the test sample to which the DPD "total chlorine" test reagent was added. The light shield is then closed as was done for the blank, and the READ key is depressed. The result, in mg/L $Cl_2$ is shown on the display within a few seconds. This is the "total chlorine" level of the water sample under investigation.
3. To convert "total chlorine" to "total bromine" the value obtained for "total chlorine" should be multiplied by 2.25. Total bromine is, in the case of the microbiocides used in the practice of this invention, the same as active bromine.

The duration of the period during which an animal drinking water composition of this invention is made available to the animal(s) can be varied, depending upon such factors as the type, size and age of the animal(s) and the identity of the particular microbiocide being used pursuant to this invention. Typically, with fowl such as chickens, ducks, geese, or turkeys entirely satisfactory reductions in fecal microbiological contamination may be achieved within periods of about 1 to about 10 days after making the treated drinking water continuously available to the fowl. On the other hand with larger animal species such as cattle, sheep, or swine, beneficial reductions in fecal microbiological contamination may be achieved in periods in the range of about 1 to about 30 days after making the treated drinking water continuously available to such animals. In the case of animal harvesting, usually the drinking water treated pursuant to this invention will be provided to the animal(s) for a period just prior to slaughter. However, it is possible to provide the treated drinking water of this invention to animal(s) which are not to be slaughtered, such as dairy cows, egg-producing hens, horses, mules, or donkeys, as well as domestic animals such as cats, dogs, and rabbits, as well as zoo animals and animals in the wild such as deer, ducks, geese, and wild turkeys. In these situations the bacterial count of fecal matter from the animal can be controlled.

In providing a drinking water composition of this invention to an animal, various regimes can be used. In the case of processing of animals for meat products, typically the period of availability of the treated water will directly precede slaughter. However, if desired, an intermediate period can be provided during which ordinary drinking water is furnished to the animal before slaughter. Other regimes can be used especially where the animal is not to be slaughtered. Here it is possible to periodically furnish the animal a drinking water of this invention for short periods of time in between periods where the animal is provided with ordinary drinking water not treated pursuant to this invention.

The microbiocides introduced into water to form animal drinking water compositions of this invention can be used alone or in combination with one or more other microbiocides suitable for use in the drinking water of the animal, such as for example Aquatize® biocide (Bioxy Incorporated, 3733 National Drive, Suite 115, Raleigh, N.C. 27612-4845), sodium hypochlorite (Clorox® bleach), Alcide® biocide (Alcide Corporation, 125 Main St. Westport Conn.), and ozone which is available from various suppliers.

The practice and advantages of this invention are illustrated by the following non-limiting Examples.

EXAMPLE 1

Comparative tests were conducted to determine the effect, if any, on the fecal bacteria counts of broilers receiving dosages of several different microbiocidal compositions. These compositions were administered to female broilers via drinking water during the both the last day of feed consumption and an ensuing 9-hour period of feed withdrawal (i.e., during a total period of 33 hours prior to processing). The test period began when broilers were 56 days of age and continued through the 9-hour feed withdrawal period. A total of 100 birds of a chick strain were housed at hatch and used in the tests. Each test group contained 10 female broilers randomly assigned into a given replicate group containing 10 female broilers per group. Ten test groups were employed. Sacrificial processing of the broilers began immediately after the end of the 9-hour period. Food and water consumption during the test period were determined. In addition, fecal bacteria and ending intestine condition were measured at the end of the 9 hours of feed withdrawal.

The biocides tested were Aquatize® biocide (Bioxy Incorporated), sodium hypochlorite (Clorox® bleach), and 1,3-dibromo-5,5-dimethylhydantoin (hereinafter sometimes referred to as DBDMH. Table 1 shows the experimental design used in these tests. The microbiocides used in these tests were used only in the final 24-hour period during which for consumption was present and during the ensuing 9-hour period of feed withdrawal, the 33-hour period.

TABLE 1

| Test Group | Microbiocide Tested (During the 33-hour period) | Replicates | Chicks per Replicate |
|---|---|---|---|
| 1 | None | One | 10 |
| 2 | Clorox ® solution (6 ppm Cl$_2$ equivalent) | One | 10 |
| 3 | Aquatize ® biocide 1:1000 (vol:vol) | One | 10 |
| 4 | Aquatize ® biocide 1:1000 (vol:vol) plus citric acid (0.015% of total solution) | One | 10 |
| 5 | 40% NaBr solution 1:1000 (vol:vol) plus Clorox ® solution (1:3500 dilution) | One | 10 |
| 6 | 40% NaBr solution 1:2000 (vol:vol) plus Clorox ® solution (1:1750 dilution) | One | 10 |
| 7 | 40% NaBr solution 1:4000 (vol:vol) plus Clorox ® solution (1:1200 dilution) | One | 10 |
| 8 | DBDMH (5 ppm Cl$_2$ equivalent) | One | 10 |
| 9 | DBDMH (10 ppm Cl$_2$ equivalent) | One | 10 |
| 10 | DBDMH (15 ppm Cl$_2$ equivalent) | One | 10 |

The drinking water solutions of 1,3-dibromo-5,5-dimethylhydantoin of this invention formed using the following procedure. A stock solution of DBDMH was prepared by stirring 100 g of DBDMH into 10 liters (10,000 mL) of water for 20 minutes. After filtration, the resulting clear solution contains 1300 mg per liter as Br$_2$. This corresponds to 580 mg per liter (or 580 ppm Cl$_2$ when expressed as Cl$_2$. The diluted solutions of DBDMH used in these tests were then formed as follows:

1) To prepare the DBDMH test solution having 5 ppm Cl$_2$ equivalent, a total of 87.5 mL of the above stock solution was added to and mixed with 10 liters (10,000 mL) of prepared chicken chill water solution.
2) To prepare the DBDMH test solution having 10 ppm Cl$_2$ equivalent, a total of 175.0 mL of the above stock solution was added to and mixed with 10 liters (10,000 mL) of prepared chicken chill water solution.
3) To prepare the DBDMH test solution having 15 ppm Cl$_2$ equivalent, a total of 262.5 mL of the above stock solution was added to and mixed with 10 liters (10,000 mL) of prepared chicken chill water solution.

The following test protocol was used in the tests:

a. The appropriate groups of birds at 55 days of age were placed in separate pens with water and litter contaminated with *E. coli*.

b. Test solutions of Aquatize® biocide, sodium hypochlorite solution (Clorox® bleach), NaBr solution activated by hypochlorite, or DBDMH were placed in appropriate pens as drinking water source (contaminated with *E. coli*) offered ad libitum for the last 33 hours prior to processing (i.e., the 24-hour period of feed consumption followed by a 9-hour feed withdrawal period).

c. After the 24-hour period of feed consumption, the feed was withdrawn from all treatment groups. Water consumption, including treatment groups, was allowed to continue for the next 9 hours.

d. After the next 9 hours, 10 birds per pen were dispatched and the small intestine gut contents were collected for fecal material bacteria evaluation. The gut contents were collected by squeezing the gut; the gut was not scraped.

e. Water consumption during the 9-hour feed withdrawal period was measured.

f. Small intestine condition (i.e., redness) was rated after gut fecal collection.

g. All the contents for each of the respective pens were placed into a single container for that particular pen.

h. Fecal bacteria evaluation of fecal material for the respective pens was then conducted.

Table 2 summarizes the results of this group of tests in terms of change in water consumption in the final 33-hour period and the mean fecal bacteria reduction resulting from use of the respective microbiocidal compositions.

TABLE 2

| Test Group | Microbiocide Tested | Change in Water Consumption | Mean Fecal Bacteria Reduction |
|---|---|---|---|
| 1 | None | Control | Control |
| 2 | Clorox ® solution (6 ppm Cl$_2$ equivalent) | (24.2%) | 11.1% |
| 3 | Aquatize ® biocide 1:1000 (vol:vol) | (3.5%) | 78.6% |
| 4 | Aquatize ® biocide 1:1000 (vol:vol) plus citric acid (0.015% of total solution) | (7.8%) | 92.4% |
| 5 | 40% NaBr solution 1:1000 (vol:vol) plus Clorox ® solution (1:3500 dilution) | (5.1%) | 63.7% |
| 6 | 40% NaBr solution 1:2000 (vol:vol) plus Clorox ® solution (1:1750 dilution) | (16.0%) | 72.3% |
| 7 | 40% NaBr solution 1:4000 (vol:vol) plus Clorox ® solution (1:1200 dilution) | (19.7%) | 96.0% |
| 8 | DBDMH (5 ppm Cl$_2$ equivalent) | 1.9% | 92.6% |
| 9 | DBDMH (10 ppm Cl$_2$ equivalent) | 2.1% | 99.9999% |
| 10 | DBDMH (15 ppm Cl$_2$ equivalent) | (0.3%) | 99.9999% |

EXAMPLE 2

The procedure of Example 1 was repeated except that the experimental design set in Table 3 was used.

TABLE 3

| Test Group | Microbiocide Tested (During the 33-hour period) | Replicates | Chicks per Replicate |
|---|---|---|---|
| 1 | None | Five | 40 |
| 2 | Clorox solution (4 ppm $Cl_2$ equivalent) | Five | 40 |
| 3 | Aquatize ® biocide 1:1000 (vol:vol) | Five | 40 |
| 4 | Aquatize ® biocide 1:2000 (vol:vol) | Five | 40 |
| 5 | Aquatize ® biocide 1:3000 (vol:vol) | Five | 40 |
| 6 | Aquatize ® biocide 1:5000 (vol:vol) | Five | 40 |
| 7 | DBDMH (3 ppm $Cl_2$ equivalent) | Five | 40 |
| 8 | DBDMH (7.5 ppm $Cl_2$ equivalent) | Five | 40 |
| 9 | DBDMH (10 ppm $Cl_2$ equivalent) | Five | 40 |

The solutions of 1,3-dibromo-5,5-dimethylhydantoin of this invention were formed using the following procedure. A stock solution of DBDMH was prepared by stirring 100 g of DBDMH into 10 liters (10,000 mL) of water for 20 minutes. After filtration, the resulting clear solution contains 1300 mg per liter as $Br_2$. This corresponds to 580 mg per liter (or 580 ppm $Cl_2$ when expressed as $Cl_2$.) The diluted solutions of DBDMH used in these tests were then formed as follows:

1) To prepare the DBDMH test solution having 3 ppm $Cl_2$ equivalent, a total of 52.5 mL of the above stock solution was added to and mixed with 10 liters (10,000 mL) of prepared chicken chill water solution.
2) To prepare the DBDMH test solution having 7.5 ppm $Cl_2$ equivalent, a total of 126.25 mL of the above stock solution was added to and mixed with 10 liters (10,000 mL) of prepared chicken chill water solution.
3) To prepare the DBDMH test solution having 10 ppm $Cl_2$ equivalent, a total of 175.0 mL of the above stock solution was added to and mixed with 10 liters (10,000 mL) of prepared chicken chill water solution.

In addition to water consumption and mean fecal bacteria reduction as determined in Example 1, determination were also made of the mean feed consumption in terms of grams per bird during the final 24-hour period of feed availability before slaughter. In addition, visual observations were made of intestinal redness of the dispatched fowl. The intestinal redness scale used was as follows: 0=small intestine is clear; 1=less than one-third is red; 2=between one-third and one-half of the intestine is red; 3=more than one-half of the intestine is red.

Tables 4 and 5 summarize the results of these tests. In Table 4 the change in water consumption is that occurring in the 33-hour period prior to slaughter. In Table 5 the mean consumption is in terms of grams per bird during the final 24-hour period during which was available to the birds.

TABLE 4

| Test Group | Microbiocide Tested | Change in Water Consumption | Mean Fecal Bacteria Reduction |
|---|---|---|---|
| 1 | None | Control | Control |
| 2 | Clorox solution (4 ppm $Cl_2$ equivalent) | (32.3%) | 66.8% |
| 3 | Aquatize ® biocide 1:1000 (vol:vol) | (19.6%) | 91.3% |
| 4 | Aquatize ® biocide 1:2000 (vol:vol) | (1.8%) | 79.2% |
| 5 | Aquatize ® biocide 1:3000 (vol:vol) | (3.2%) | 68.4% |
| 6 | Aquatize ® biocide 1:5000 (vol:vol) | 2.1% | 61.1% |
| 7 | DBDMH (3 ppm $Cl_2$ equivalent) | 1.3% | 89.6% |
| 8 | DBDMH (7.5 ppm $Cl_2$ equivalent) | 0.3% | 99.9999% |
| 9 | DBDMH (10 ppm $Cl_2$ equivalent) | (0.9%) | 99.9999% |

TABLE 5

| Test Group | Microbiocide Tested | Mean Feed Consumption, g/bird | Intestinal Redness Measurement |
|---|---|---|---|
| 1 | None | 197 | 0.3 |
| 2 | Clorox solution (4 ppm $Cl_2$ equivalent) | 152 | 2.2 |
| 3 | Aquatize ® biocide 1:1000 (vol:vol) | 173 | 0.8 |
| 4 | Aquatize ® biocide 1:2000 (vol:vol) | 196 | 0.4 |
| 5 | Aquatize ® biocide 1:3000 (vol:vol) | 205 | 0.5 |
| 6 | Aquatize ® biocide 1:5000 (vol:vol) | 198 | 0.1 |
| 7 | DBDMH (3 ppm $Cl_2$ equivalent) | 199 | 0.3 |
| 8 | DBDMH (7.5 ppm $Cl_2$ equivalent) | 206 | 0.5 |
| 9 | DBDMH (10 ppm $Cl_2$ equivalent) | 204 | 0.4 |

EXAMPLE 3

Comparative tests were conducted to determine the fecal bacteria counts, if any, of beef steers reared in a feedlot setting and receiving either no disinfecting agent, Aquatize® biocide, sodium hypochlorite solution (Clorox Bleach), or 1,3-dibromo-5,5-dimethylhydantoin (DBDMH) administered via drinking water when administered the last two days of feed consumption (48 hours prior to processing). A total of 15 beef steers weighing 800–950 pounds housed in individual pens were used in the study. These steers were offered normal drinking water with either no disinfecting agent (Control), or specified dosages of Aquatize®, Clorox Bleach, or DBDMH. Each drinking water solution (contaminated with *E. coli*) was offered continuously ad libitum during the 48-hour period, at which time fecal sample collection occurred. The fecal material samples were taken by anal swab from each steer for total fecal bacteria evaluation. Food consumption, water consumption, fecal bacteria, and ending intestine condition were measured at the end of the study. Each group of steers treated with a given biocide consisted of 5 steers, thus providing five replicates for a total number of 15 animals on study (plus controls). Table 6 shows the experimental design used in these tests.

TABLE 6

| Test Group | Test Material (During 24 hr feed consumption + 9 hr feed withdrawal) | Reps | Beef Steers/Rep |
|---|---|---|---|
| 1 | None | 5 | One (1) |
| 2 | Clorox (or 4 ppm $Cl_2$ equivalent) | 5 | One (1) |

TABLE 6-continued

| Test Group | Test Material (During 24 hr feed consumption + 9 hr feed withdrawal) | Reps | Beef Steers/Rep |
|---|---|---|---|
| 3 | Aquatize ® (1:1000 dilution rate) | 5 | One (1) |
| 4 | DBDMH (7.5 ppm $Cl_2$ equivalent) | 5 | One (1) |

The results of these tests are summarized in Table 7.

TABLE 7

| Water Treatment[1] | Average Water Consumption (% Change) | Average Fecal Bacteria (% Reduction) | Feed Consumption Reduction (post 48 hr Water Treatment) |
|---|---|---|---|
| None (Control) | — | — | — |
| Clorox (3 ppm $Cl_2$) | 18% | 31% | −18% |
| Aquatize ® (1:1000 dilution rate) | 22% | 55% | −9% |
| DBDMH (7.5 ppm) | 2% | 92% | −2% |

EXAMPLE 4

Comparative tests were conducted to determine the fecal bacteria counts, if any, of swine reared in a typical commercial setting and receiving either no disinfecting agent, Aquatize® biocide, sodium hypochlorite solution (Clorox bleach), or 1,3-dibromo-5,5-dimethylhydantoin (DBDMH) administered via drinking water when administered the last two days of feed consumption (48 hours prior to processing). A total 15 pigs weighing 230–250 pounds each housed in individual pens were used in the study. The pigs were offered normal drinking water with either no disinfecting agent (Control), or specified dosages of Aquatize®, Clorox bleach, or DBDMH. Each drinking water solution (contaminated with E. coli) was offered continuously ad libitum during the 48-hour period, at which time fecal sample collection occurred. The fecal material samples were taken by anal swab from each pig for total fecal bacteria evaluation. Food consumption, water consumption, fecal bacteria, and ending intestine condition were measured at the end of the study. Each group of pigs treated with a given biocide consisted of 5 replicates of 1 pig per replicate for a total of 5 animals in each test group. Table 8 describes the experimental design of these tests.

TABLE 8

| Test Group | Test Material (During 24 hr feed consumption + 9 hr feed withdrawal) | Reps | Pigs/Rep |
|---|---|---|---|
| 1 | None | 5 | One (1) |
| 2 | Clorox (or 4 ppm $Cl_2$ equivalent) | 5 | One (1) |
| 3 | Aquatize ® (1:1000 dilution rate) | 5 | One (1) |
| 4 | Aquatize ® (1:2000 dilution rate) | 5 | One (1) |
| 5 | Aquatize ® (1:3000 dilution rate) | 5 | One (1) |
| 6 | Aquatize ® (1:5000 dilution rate) | 5 | One (1) |
| 7 | DBDMH (3 ppm $Cl_2$ equivalent) | 5 | One (1) |
| 8 | DBDMH (7.5 ppm $Cl_2$ equivalent) | 5 | One (1) |

Table 9 summarizes the results of this study.

TABLE 9

| Water Treatment | Average Water Consumption (% Change) | Average Fecal Bacteria Reduction (%) |
|---|---|---|
| None (Control) | — | — |
| Clorox (or 4 ppm $Cl_2$ equivalent) | −41% | 55% |
| Aquatize ® (1:1000 dilution rate) | −9% | 87% |
| Aquatize ® (1:2000 dilution rate) | −4% | 61% |
| Aquatize ® (1:3000 dilution rate) | −2% | 45% |
| Aquatize ® (1:5000 dilution rate) | −3% | 32% |
| DBDMH (3 ppm $Cl_2$ equivalent) | −1% | 82% |
| DBDMH (7.5 ppm $Cl_2$ equivalent) | −4% | 96% |

EXAMPLE 5

A study was made to determine the efficacy and safety of various drinking water treatments provided to immature broilers housed in battery cages for 21 days. In these tests, the drinking water for newly hatched chicks was treated with various chemicals and the chicks were provided with drinking water from given supply of a given treated water for a period of 21 days. Upon completion of the study, birds were examined for differences, if any, in body weight gain, feed efficiency, and fecal bacteria counts resulting from use of the various water treatments. Potential mortality was the key measure of safety. This study was conducted in compliance with the Food and Drug Administration's Good Laboratory Practices regulations (21 CFR Part 58), Adequate and Well-Controlled Studies (21 CFR Part 514.117), New Animal Drugs for Investigational Use (21 CFR Part 511), and CVM Guidelines for Conduct of Clinical Investigations: Responsibilities of Clinical Investigators and Monitors for Investigational New Animal Drug Studies, October, 1992. The chemicals added to the respective sources of the drinking water were hypochlorite solution (Clorox bleach), 1,3-dibromo-5,5-dimethylhydantoin (DBDMH; Albemarle Corporation), N,N'-bromochloro-5,5-dimethylhydantoin (often referred to herein as BCDMH), and sulfamate stabilized bromine chloride (often referred to herein as SSBC) (Stabrom® 909 biocide; Albemarle Corporation).

The test was initiated with 1040 healthy chicks (approximately 50% being males and 50% being females). The birds were weighed and randomly placed in cages at hatch. E. Coli was administered to the birds at hatch to 3 days post hatch via drinking water treatment (Os inoculation) using a grown live culture of $10^5$ E. Coli per mL of drinking water. The test materials in the drinking water were administered for the total test period of 21 days. Twelve treatment groups plus a control group were fed for 21 days, not counting any mortality which occurred.

A common commercial basal starter feed devoid of coccidiostats and antibiotics was administered ad libitum for the duration of the trial, with all chicks fed the same diets. No medications such as arsenicals, and no vaccinations were given during the entire experimental feeding period composed of day of hatch to day 21 post hatch.

The test groups used in this study are identified in Table 10.

TABLE 10

| Test Group | Test Material | Test Material Level | No. of Blocks | No. of Broilers per Block | Total Broiler per Test Group |
|---|---|---|---|---|---|
| 1 | None (Control) | N/A | 8 | 10 (5M + 5F) | 80 |
| 2 | Clorox (Bleach) | 4 ppm $Cl_2$ equivalent | 8 | 10 (5M + 5F) | 80 |
| 3 | Clorox (Bleach) | 8 ppm $Cl_2$ equivalent | 8 | 10 (5M + 5F) | 80 |
| 4 | Clorox (Bleach) | 12 ppm $Cl_2$ equivalent | 8 | 10 (5M + 5F) | 80 |
| 5 | DBDMH (SBS1021) | 4 ppm $Cl_2$ equivalent | 8 | 10 (5M + 5F) | 80 |
| 6 | DBDMH (SBS1021) | 8 ppm $Cl_2$ equivalent | 8 | 10 (5M + 5F) | 80 |
| 7 | DBDMH (SBS1021) | 12 ppm $Cl_2$ equivalent | 8 | 10 (5M + 5F) | 80 |
| 8 | BCDMH (Brom Tabs) | 4 ppm $Cl_2$ equivalent* | 8 | 10 (5M + 5F) | 80 |
| 9 | BCDMH (Brom Tabs) | 8 ppm $Cl_2$ equivalent* | 8 | 10 (5M + 5F) | 80 |
| 10 | BCDMH (Brom Tabs) | 12 ppm $Cl_2$ equivalent* | 8 | 10 (5M + 5F) | 80 |
| 11 | SSBC | 4 ppm $Cl_2$ equivalent | 8 | 10 (5M + 5F) | 80 |
| 12 | SSBC | 8 ppm $Cl_2$ equivalent | 8 | 10 (5M + 5F) | 80 |
| 13 | SSBC | 12 ppm $Cl_2$ equivalent | 8 | 10 (5M + 5F) | 80 |
| TOTAL | | | 8/treatment | 10/block | 1040 |

*Based on bromine content only. Actually the true halogen content was twice that reported.

The procedures used in forming the drinking water solutions identified in Table 10 were as follows:

a) Clorox bleach solutions—to maintain an accurate $Cl_2$ equivalent, 20.0 g of Clorox (5.25% NaOCl) was stirred into 1 liter of de-ionized water to create a stock solution. For 4 ppm $Cl_2$ equivalent, 4 mL of stock solution was added to and mixed with 1 liter of water. For 8 ppm $Cl_2$ equivalent, 8 mL of stock solution was added to and mixed with 1 liter of water. For 12 ppm $Cl_2$ equivalent, 12 mL of stock solution was added to and mixed with 1 liter of water.

b) DBDMH—to maintain an accurate $Cl_2$ equivalent, 10.0 g of DBDMH was and stirred into 1 liter of de-ionized water to create a stock solution which was mixed well for at least 20 minutes. Not all of the DBDMH dissolved, but the resultant solids-containing solution was a saturated solution. In forming the test drinking water solutions, gravity filtration was employed so as to filter off the insolubles. For 4 ppm $Cl_2$ equivalent, 7.0 mL of stock solution was mixed with 1 liter of water. For 8 ppm $Cl_2$ equivalent, 14.0 mL of stock solution was mixed with 1 liter of water. For 12 ppm $Cl_2$ equivalent, 21.0 mL of stock solution was mixed with 1 liter of water.

c) BCDMH (Brom Tabs; obtained from N. Jonas & Co., Inc.)—to maintain an accurate $Cl_2$ equivalent, 10.0 g of BCDMH was stirred into 1 liter of de-ionized water to create a stock solution and mixed well for at least 20 minutes. Not all of the BCDMH dissolved, but the resultant solids-containing solution was a saturated solution. In forming the test drinking water solutions, gravity filtration was employed to filter off the insolubles. For 4 ppm $Cl_2$ equivalent, 7.0 mL of stock solution was mixed with 1 liter of water. For 8 ppm $Cl_2$ equivalent, 14.0 mL of stock solution was mixed with 1 liter of water. For 12 ppm $Cl_2$ equivalent, 21.0 mL of stock solution was mixed with 1 liter of water.

d) SSBC—to maintain an accurate $Cl_2$ equivalent, 14.4 g of Stabrom® 909 biocide solution was stirred into 1 liter of de-ionized water to create a stock solution. For 4 ppm $Cl_2$ equivalent, 4 mL of stock solution was mixed with 1 liter of water. For 8 ppm $Cl_2$ equivalent, 8 mL of stock solution was mixed with 11 liter of water. For 12 ppm $Cl_2$ equivalent, 12 mL of stock solution was mixed with 1 liter of water.

On day of hatch the mean body weights of the treatment groups were compared to the control group. Groups with mean weights greater or less than one standard deviation of the mean control group were subjected to another randomization to assure equal distribution of weight among all of the groups tested. The broiler chicks were housed in battery cages. In all, 39 cages were used in this test. Each cage served as an experimental unit. The cages were located in a room of wood/cinder block structure with metal roof and low ceiling insulated to R value of 19 for the roof and 12 for the side walls. No cage touched any other cage from the side so as to ensure prevention of cross-contamination. Each cage was a separate free-standing cage, and the cages were separated by a wire partition. A cross-house ventilation system and ceiling fans were evenly spaced in the wood/cinder block structure. Room humidity was not monitored. Warm room brooding was provided using forced air heaters during day of hatch to day 21 post hatch. Also, continuous 24-hour lighting was provided by means of incandescent lights. Cages, aisles, feeders and waterers were sanitized prior to bird placement on day of hatch. Because no contaminants that could interfere with study objectives are expected in the feed, no assays for potential contaminants were performed. Drinking water for use by the respective test groups was provided ad libitum at all times. The facility tap water was supplied via well and subjected to regulation by the U.S. Environmental Protection Agency. Water supplied to the test facilities was subject to quarterly analyses for mercury, lead, conductivity, pH, fluoride and coliform. Since no contaminants that might interfere with study objectives were expected to occur in the water, no assays for other potential contaminants were performed.

The observations, tests and measurements used were as follows:

a) Broilers were observed three times daily beginning on day of hatch to determine mortality or the onset, severity, and duration of any behavioral changes or evidence of toxicity (including fecal material condition, presence of diarrhea, nervousness, accessibility to water and feed, general bird appearance, and any adverse conditions which should affect performance).

b) Any unusual observations were recorded and confirmed by a veterinarian.

c) On Trial Day 21, body weights were taken by weighing individual broilers in a cage and recorded. Body weight gain was calculated by determining actual body weight gain (ending minus beginning weights) during the period of day of hatch to day 21 post hatch.

d) During day of hatch to day 21 post hatch, mortality was observed daily and reported as percentage per time period.

e) Food consumption was evaluated for each cage for the entire trial (day of hatch to day 21 post hatch). A separate container (feed trough) was assigned for each cage.

f) The initial tare weight for each feed trough was recorded on day of hatch. Feed was added and the weight recorded.

g) Prior to adding feed, the feed trough was weighed and the weight recorded (Weight out). Feed out means feed that is removed and taken out of the calculations. New feed was added and the weight recorded (Weight in).

h) Any feed that may have been inadvertently spilled during the course of the study was noted on the daily observation sheet. Feed spilled was weighed (weights recorded on appropriate forms) and discarded and thus not used for further consumption.

i) Feed consumption was calculated as feed consumption divided by body weight gain for each period {calculated for both ending minus mortality body weight gain and ending body weight plus mortality body weight gain}.

j) Statistical evaluations involved use of randomized block (Power of the test to detect a 5% difference from the mean using a alpha of 0.05 and a beta of 0.20–0.25). Block may include gender and/or location.

k) Temperature (at bird height) was observed and recorded three times per day (one reading per house). A temperature of 85±5° F. or within the limits of facility (if environmental temperature rises above 85° F. this temperature may rise above) was maintained for the first week and reduced 1° F. per day until 70° F. is reached.

l) A determination of total fecal bacteria was conducted at trial day 21 or age.

m) All birds were sacrificed on trial day 21.

n) Necropsy examinations were performed during the study by qualified personnel on all broilers found dead or moribund. All animals placed on study were gross necropsied and observations were recorded.

o) Bacteria count determination: At time of necropsy, a fecal sample from the gut of each bird was taken and pooled with fecal samples of all birds from that cage only (4 samples pooled minus mortality) and placed in plastic sample bags. A swab was dipped into the combined fecal pool for each cage and stirred into the entire mixture. The excess fecal material on the swab was taken off by using the inside of the bag from which the fecal sample came, and wiping off the excess. The swab was then be stirred into a syringe with 5 mL of distilled water. Each of these samples was placed on MacConkey Agar plates (3-sectioned plates) by dropping 0.1 mL of finished solution into a section of the plate. The plates were marked by treatment type and each section was marked by unit number (cage number). Each of the 3 replications for each treatment was placed into the same agar plate, but into the 3 different sections for each replicate. The plates were incubated overnight for approximately 12 hours at 37° C. The CFU's (Colony Forming Units) were then observed and the count recorded.

p) Records were maintained of period observations, daily mortality and clinical observations, body weights, environmental monitoring records for the animal facility, environmental monitoring records for the test article and diet storage areas, feed consumption, test article accountability, animal receipt and source records, necropsy data, protocol and amendments, SOP and protocol deviations, chain of custody records for all specimens and samples generated.

Data generated during the study was subjected to the following statistical tests: For all parameters, the multifactorial procedure was used to compare means of treatment groups, using ANOVA (Analysis of Variance). Means will further be separated using Least Significant Difference.

Table 11 summarizes the results of this series of tests.

TABLE 11

Live Animal Performance (1–21 days of age)[1]

| Test Material | Mean Body Wt. (g) | Feed Conversion | Mortality (%) | Feed 21-day Bacteria (% change from control) |
|---|---|---|---|---|
| None (Control) | 683.4 cde | 1.317 ab | 5.00 ab | — |
| Bleach - 4 ppm $Cl_2$ equivalent | 676.5 ef | 1.314 ab | 6.25 ab | 28 |
| Bleach - 8 ppm $Cl_2$ equivalent | 664.0 fg | 1.335 b | 10.00 bc | 68 |
| Bleach - 12 ppm $Cl_2$ equivalent | 647.0 g | 1.373 c | 13.75 c | 66 |
| DBDMH - 4 ppm $Cl_2$ equivalent | 697.9 abcd | 1.322 ab | 2.50 a | 85 |
| DBDMH - 8 ppm $Cl_2$ equivalent | 709.4 ab | 1.300 ab | 5.00 ab | 97 |
| DBDMH - 12 ppm $Cl_2$ equivalent | 711.1 a | 1.287 a | 5.00 ab | 99 |
| BCDMH - 4 ppm $Cl_2$ equivalent | 680.5 def | 1.315 ab | 2.50 a | 45 |
| BCDMH - 8 ppm $Cl_2$ equivalent | 690.9 bcde | 1.312 ab | 5.00 ab | 73 |
| BCDMH - 12 ppm $Cl_2$ equivalent | 697.0 abcd | 1.301 ab | 3.75 a | 83 |
| SSBC - 4 ppm $Cl_2$ equivalent | 677.5 ef | 1.321 ab | 6.25 ab | 66 |
| SSBC - 8 ppm $Cl_2$ equivalent | 682.9 efg | 1.322 ab | 6.25 ab | 79 |
| SSBC - 12 ppm $Cl_2$ equivalent | 702.4 abc | 1.300 ab | 5.00 ab | 92 |

[1]NOTE:
Means within a row without a common superscript are significantly different (P < 0.05) as determined by Least Significant Difference.

It can be seen from Table 11 that:
1) DBDMH, BCDMH, and SSBC were all found to be safe to administer to baby chicks (i.e., they did not create excessive mortality and weight gain loss).
2) Body weights appeared to be larger when either DBDMH (8 or 12 ppm) or SSBC (12 ppm) were administered.
3) DBDMH administered at either 8 or 12 ppm appreciably reduced fecal bacteria to 96–99% total bacteria reduction.

Table 12 summarizes in tabular form the schedule of events which took place during the experimental program of Example 5. Tables 13 through 15 present and summarize the data from the experimental program of Example 5 in greater detail. In Tables 13–15 bleach is sodium hypochlorite, DBDMH is 1,3-dibromo-5,5-dimethylhydantoin, BCDMH is N,N'-bromochloro-5,5-dimethylhydantoin, and SSBC is active bromine formed from bromine chloride, sodium sulfamate, and sodium hydroxide in water (Stabrom® 909 biocide).

TABLE 12

Schedule of Events

| DESCRIPTION | | Day of Hatch |
|---|---|---|
| Collect group body weights in grams by band or leg number | X | X |
| Start of test feeds | X | |
| Starter Feed Period starts | X | |
| End Experimental Feeding | | X |
| Daily Observations (each day) | X | X |
| Room Temperature (three times per day) | X | X |
| Average Body Weight determination | X | X |
| Food Consumption | | X |
| Mortality Ending (period ends) | | X |
| Daily Gain Ending | | X |

TABLE 12-continued

Schedule of Events

| DESCRIPTION | Day of Hatch |
|---|---|
| Feed Conversion Ending | X |
| Mortality: day of hatch to day 21 post hatch | x |
| Fecal Bacteria Count Determination | X |
| End of Trial | X |
| Test Material and Finished Feed Inventory: Test material remaining, finished feed not consumed, and finished feed in final storage will disposed of by burying in a private landfill | X |

TABLE 13

Body Weight Gain in Grams of Immature Broilers During the 21-day Test Period

| | Composition Tested | | | | | | |
|---|---|---|---|---|---|---|---|
| | 1 | 2 | 3 | 4 | 5 | 6 | 7 |
| Biocide | None | Bleach | Bleach | Bleach | DBDMH | DBDMH | DBDMH |
| Amount, $Cl_2$ eq. | None | 4 ppm | 8 ppm | 12 ppm | 4 ppm | 8 ppm | 12 ppm |
| Rep 1 | 667 | 658 | 654 | 620 | 708 | 695 | 703 |
| Rep 2 | 690 | 693 | 685 | 652 | 687 | 726 | 728 |
| Rep 3 | 706 | 688 | 680 | 630 | 701 | 686 | 744 |
| Rep 4 | 673 | 663 | 650 | 672 | 677 | 697 | 710 |
| Rep 5 | 663 | 672 | 649 | 668 | 722 | 714 | 699 |
| Rep 6 | 700 | 702 | 670 | 639 | 718 | 713 | 693 |
| Rep 7 | 690 | 663 | 683 | 637 | 686 | 704 | 681 |
| Rep 8 | 678 | 673 | 641 | 658 | 684 | 740 | 731 |
| Mean | 683.4 | 676.5 | 664.0 | 647.0 | 697.9 | 709.4 | 711.1 |
| STAT* | cde | ef | fg | g | abcd | ab | a |
| S.D. | 14.56 | 14.97 | 16.37 | 17.30 | 15.76 | 16.52 | 20.03 |
| C.V. | 2.13 | 2.21 | 2.47 | 2.67 | 2.26 | 2.33 | 2.82 |

| | Composition Tested | | | | | | Rep |
|---|---|---|---|---|---|---|---|
| | 8 | 9 | 10 | 11 | 12 | 13 | Mean |
| Biocide | BCDMH | BCDMH | BCDMH | SSBC | SSBC | SSBC | |
| Amount, $Cl_2$ eq. | 4 ppm* | 8 ppm* | 12 ppm* | 4 ppm | 8 ppm | 12 ppm | |
| Rep 1 | 678 | 700 | 671 | 705 | 675 | 718 | 680.92 |
| Rep 2 | 670 | 714 | 711 | 661 | 699 | 678 | 691.85 |
| Rep 3 | 680 | 670 | 692 | 650 | 715 | 674 | 685.85 |
| Rep 4 | 710 | 658 | 682 | 697 | 682 | 726 | 684.38 |
| Rep 5 | 671 | 706 | 722 | 674 | 671 | 710 | 687.77 |
| Rep 6 | 650 | 673 | 703 | 695 | 665 | 711 | 687.08 |
| Rep 7 | 700 | 712 | 702 | 678 | 654 | 677 | 682.08 |
| Rep 8 | 685 | 694 | 693 | 660 | 702 | 725 | 689.54 |
| Mean | 680.5 | 690.6 | 697.0 | 677.5 | 682.9 | 702.4 | |
| STAT* | def | bcde | abcd | ef | def | abc | |
| S.D. | 17.35 | 19.81 | 15.10 | 18.67 | 19.81 | 20.89 | |
| C.V. | 2.55 | 2.87 | 2.17 | 2.76 | 2.84 | 2.97 | |

*Based on bromine content only. Actually the true halogen content was twice that reported.
NOTE: Means within a row without a common "STAT" designation are significantly different ($P < 0.05$) as determined by Least Significant Difference.

TABLE 14

Feed Conversion (Feed:Gain Value) With Immature Broilers During the 21-day Test Period

| | Composition Tested | | | | | | |
|---|---|---|---|---|---|---|---|
| | 1 | 2 | 3 | 4 | 5 | 6 | 7 |
| Biocide | None | Bleach | Bleach | Bleach | DBDMH | DBDMH | DBDMH |
| Amount, $Cl_2$ eq. | None | 4 ppm | 8 ppm | 12 ppm | 4 ppm | 8 ppm | 12 ppm |
| Rep 1 | 1.307 | 1.285 | 1.327 | 1.428 | 1.329 | 1.373 | 1.289 |
| Rep 2 | 1.304 | 1.324 | 1.367 | 1.363 | 1.307 | 1.296 | 1.255 |
| Rep 3 | 1.347 | 1.309 | 1.333 | 1.342 | 1.384 | 1.257 | 1.321 |

TABLE 14-continued

Feed Conversion (Feed:Gain Value) With Immature Broilers During the 21-day Test Period

| | | | | | | | |
|---|---|---|---|---|---|---|---|
| Rep 4 | 1.373 | 1.327 | 1.298 | 1.417 | 1.351 | 1.289 | 1.311 |
| Rep 5 | 1.288 | 1.386 | 1.367 | 1.397 | 1.293 | 1.277 | 1.263 |
| Rep 6 | 1.266 | 1.309 | 1.356 | 1.372 | 1.321 | 1.255 | 1.318 |
| Rep 7 | 1.358 | 1.269 | 1.307 | 1.335 | 1.287 | 1.347 | 1.258 |
| Rep 8 | 1.294 | 1.301 | 1.325 | 1.328 | 1.307 | 1.303 | 1.284 |
| Mean | 1.317 | 1.314 | 1.335 | 1.373 | 1.322 | 1.300 | 1.287 |
| STAT* | ab | ab | b | c | ab | ab | a |
| S.D. | 0.04 | 0.03 | 0.02 | 0.04 | 0.03 | 0.04 | 0.03 |
| C.V. | 2.68 | 2.49 | 1.84 | 2.58 | 2.28 | 2.99 | 1.97 |

| | Composition Tested | | | | | | Rep |
|---|---|---|---|---|---|---|---|
| | 8 | 9 | 10 | 11 | 12 | 13 | Mean |
| Biocide | BCDMH | BCDMH | BCDMH | SSBC | SSBC | SSBC | |
| Amount, $Cl_2$ eq. | 4 ppm* | 8 ppm* | 12 ppm* | 4 ppm | 8 ppm | 12 ppm | |
| Rep 1 | 1.303 | 1.244 | 1.338 | 1.359 | 1.315 | 1.276 | 1.321 |
| Rep 2 | 1.361 | 1.341 | 1.308 | 1.272 | 1.281 | 1.294 | 1.313 |
| Rep 3 | 1.285 | 1.286 | 1.309 | 1.273 | 1.348 | 1.307 | 1.315 |
| Rep 4 | 1.246 | 1.352 | 1.247 | 1.318 | 1.338 | 1.273 | 1.318 |
| Rep 5 | 1.343 | 1.265 | 1.335 | 1.348 | 1.289 | 1.340 | 1.322 |
| Rep 6 | 1.345 | 1.386 | 1.280 | 1.332 | 1.313 | 1.330 | 1.322 |
| Rep 7 | 1.296 | 1.323 | 1.262 | 1.363 | 1.337 | 1.281 | 1.309 |
| Rep 8 | 1.342 | 1.302 | 1.327 | 1.300 | 1.352 | 1.299 | 1.313 |
| Mean | 1.315 | 1.312 | 1.301 | 1.321 | 1.322 | 1.300 | |
| STAT* | ab | ab | ab | ab | ab | ab | |
| S.D. | 0.04 | 0.04 | 0.03 | 0.03 | 0.02 | 0.02 | |
| C.V. | 2.78 | 3.37 | 2.46 | 2.57 | 1.88 | 1.77 | |

*Based on bromine content only. Actually the true halogen content was twice that reported.
NOTE: Means within a row without a common "STAT" designation are significantly different ($P < 0.05$) as determined by Least Significant Difference.

TABLE 15

Percentage of Mortality With Immature Broilers During the 21-day Test Period

| | Composition Tested | | | | | | |
|---|---|---|---|---|---|---|---|
| | 1 | 2 | 3 | 4 | 5 | 6 | 7 |
| Biocide | None | Bleach | Bleach | Bleach | DBDMH | DBDMH | DBDMH |
| Amount $Cl_2$ eq. | None | 4 ppm | 8 ppm | 12 ppm | 4 ppm | 8 ppm | 12 ppm |
| Rep 1 | 10.0 | 0.00 | 10.0 | 20.0 | 0.00 | 10.0 | 0.00 |
| Rep 2 | 0.00 | 10.0 | 10.0 | 10.0 | 0.00 | 0.00 | 10.0 |
| Rep 3 | 10.0 | 0.00 | 0.00 | 20.0 | 0.00 | 10.0 | 0.00 |
| Rep 4 | 0.00 | 10.0 | 10.0 | 0.00 | 0.00 | 0.00 | 10.0 |
| Rep 5 | 0.00 | 10.0 | 20.0 | 30.0 | 0.00 | 0.00 | 10.0 |
| Rep 6 | 10.0 | 10.0 | 10.0 | 10.0 | 10.0 | 0.00 | 0.00 |
| Rep 7 | 0.00 | 10.0 | 0.00 | 0.00 | 0.00 | 10.0 | 10.0 |
| Rep 8 | 10.0 | 0.00 | 20.0 | 20.0 | 10.0 | 10.0 | 0.00 |
| Mean | 5.00 | 6.25 | 10.0 | 13.75 | 2.50 | 5.00 | 5.00 |
| STAT* | ab | ab | bc | c | a | ab | ab |
| S.D. | 5.00 | 4.84 | 7.07 | 9.92 | 4.33 | 5.00 | 5.00 |
| C.V. | 100.0 | 77.5 | 70.7 | 72.2 | 173.2 | 100.0 | 100.0 |

| | Composition Tested | | | | | | Rep |
|---|---|---|---|---|---|---|---|
| | 8 | 9 | 10 | 11 | 12 | 13 | Mean |
| Biocide | BCDMH | BCDMH | BCDMH | SSBC | SSBC | SSBC | |
| Amount, $Cl_2$ eq. | 4 ppm* | 8 ppm* | 12 ppm* | 4 ppm | 8 ppm | 12 ppm | |
| Rep 1 | 10.0 | 0.00 | 0.00 | 10.0 | 0.00 | 10.0 | 6.15 |
| Rep 2 | 0.00 | 10.0 | 0.00 | 10.0 | 0.00 | 0.00 | 4.62 |
| Rep 3 | 0.00 | 10.0 | 0.00 | 10.0 | 0.00 | 10.0 | 5.38 |
| Rep 4 | 0.00 | 0.00 | 10.0 | 0.00 | 10.0 | 0.00 | 3.85 |
| Rep 5 | 10.0 | 0.00 | 10.0 | 0.00 | 10.0 | 10.0 | 8.46 |
| Rep 6 | 0.00 | 10.0 | 10.0 | 10.0 | 10.0 | 0.00 | 6.15 |
| Rep 7 | 0.00 | 10.0 | 0.00 | 10.0 | 10.0 | 0.00 | 4.62 |
| Rep 8 | 0.00 | 0.00 | 0.00 | 10.0 | 10.0 | 10.0 | 7.69 |
| Mean | 2.50 | 5.00 | 3.75 | 6.25 | 6.25 | 5.00 | |
| STAT* | a | ab | a | ab | ab | ab | |

TABLE 15-continued

Percentage of Mortality With Immature Broilers During the 21-day Test Period

| S.D. | 4.33 | 5.00 | 4.84 | 4.84 | 4.84 | 5.00 |
|---|---|---|---|---|---|---|
| C.V. | 173.2 | 100.0 | 129.1 | 77.5 | 77.5 | 100.0 |

*Based on bromine content only. Actually the true halogen content was twice that reported.
NOTE: Means within a row without a common "STAT" designation are significantly different (P < 0.05) as determined by Least Significant Difference.

While chemists understand what is meant by "aqueous" in connection with a solution or medium or the like, it is probably desirable to state for anyone who may make it a profession to quibble over every word someone uses, just what "aqueous" means. The adjective "aqueous" means that the solution or medium or whatever other noun the adjective modifies, can be water whether highly purified or of ordinary purity such as emanates from the faucet. Besides naturally-occurring trace impurities that may be present in, say, potable water in general, such as ordinary well water or municipal water, the adjective "aqueous" also permits the presence in the water of dissolved salts that are formed in the course of forming a bromine-based microbiocide in the water, e.g., by reaction between bromine chloride and sodium sulfamate in an overbased aqueous solution. Also "aqueous" permits the presence in the water of the amount of the halogen-based microbiocide itself to the extent that it may dissolve in the water, plus any dissolved reactant(s) that may remain after the reaction. Also the water may contain a few atoms that may dissolve from the vessel in which the reaction takes place, plus air-borne impurities that may find their way into the water. The point here is that the term "aqueous" does not restrict the medium or solvent to absolutely pure water—the aqueous solution or medium or the like can contain what would normally be present and/or reasonably be expected to be present in it under the particular circumstances involved when employing ordinary common sense. Nor does the term "water" denote that it must be absolutely pure; but normally water itself before being used in the practice of the invention will not contain as many things as, say, an aqueous medium in which a chemical reaction such as the reaction between bromine chloride and sodium sulfamate has taken place or in which a bromine-based microbiocide has been dissolved.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

As used herein the term "microbiocidally-effective amount" denotes that the amount used controls, kills, or otherwise reduces the bacterial or microbial content of the fecal matter of an animal by a statistically significant amount as compared to fecal matter from the same type of animal receiving the same type of feed under the same type of conditions. The term "substantially exclusive" as used hereinafter means, quite simply, that it matters not if by chance or design ordinary drinking water is given to an animal during a period when a treated drinking water of this invention is otherwise being provided to the animal, provided that the animal receives enough of the treated drinking water of this invention to result in a decrease in its fecal bacterial content. In such cases, interruptions in the administration of the drinking water of this invention to the animal are within the contemplation and scope of the present invention. Also, the term "water-soluble" merely denotes that the substance has enough solubility in water to serve its intended purpose and function. The substance need not be soluble in all proportions or even highly soluble in water.

All documents referred to herein are incorporated herein by reference in toto as if fully set forth in this document.

This invention is susceptible to considerable variation within the spirit and scope of the appended claims.

What is claimed is:

1. A method of reducing fecal contamination in an animal, which method comprises providing to the animal drinking water containing a microbiocidally-effective amount of halogen-based microbiocide resulting from mixing with water at least one 1,3-dibromo-5,5-dialkylhydantoin in which one of the alkyl groups is a methyl group and the other alkyl group contains in the range of 1 to about 4 carbon atoms.

2. A method according to claim 1 wherein said at least one 1,3-dibromo-5,5-dialkylhydantoin in the form of solids or as a water solution or slurry formed from said at least one 1,3-dibromo-5,5-dialkylhydantoin, is mixed with water and optionally the water mixture is further diluted one or more times with water, to provide said microbiocidally-effective amount of halogen-based microbiocide in said drinking water.

3. A method according to claim 1 wherein said at least one 1,3-dibromo-5,5-dialkylhydantoin before it is mixed with any water is 1,3-dibromo-5,5-dimethylhydantoin.

4. A method according to claim 1 wherein said at least one 1,3-dibromo-5,5-dimethylhydantoin before it is mixed with any water is a mixture of 1,3-dibromo-5,5-dimethylhydantoin and 1,3-dibromo-5-ethyl-5-methylhydantoin.

5. A method according to claim 3 wherein said 1,3-dibromo-5,5-dimethylhydantoin before it is mixed with any water is in the form of granules having a compression strength of at least about 15 pounds per inch and wherein said granules are devoid of any binder or other component tending increase the compression strength of the granules.

6. A method according to any of claim 1, 2, 3, 4 or 5, wherein said animal is poultry, swine, sheep, or cattle.

7. In the processing of at least one animal for at least one meat product, the improvement which comprises reducing fecal contamination in said at least one animal prior to slaughter, which method comprises providing to the animal as its exclusive or substantially exclusive source of drinking water during a period prior to slaughter, drinking water containing a microbiocidally-effective amount of halogen-based microbiocide resulting from mixing with water at least one 1,3-dibromo-5,5-dialkylhydantoin in which one of the alkyl groups is a methyl group and the other alkyl group contains in the range of 1 to about 4 carbon atoms.

8. The improvement according to claim 7 wherein said at least one animal is poultry, swine, sheep, or cattle.

9. The improvement according to claim 7 wherein said microbiocidally-effective amount of halogen-based microbiocide in said drinking water is in the range of about 1 to about 100 ppm (wt/wt) expressed as $Br_2$.

10. The improvement according to claim 7 wherein said microbiocidally-effective amount of halogen-based microbiocide in said drinking water is in the range of about 4 to about 30 ppm (wt/wt) expressed as $Br_2$.

11. The improvement according to claim 7 wherein said microbiocidally-effective amount of halogen-based microbiocide results from use of 1,3-dibromo-5,5-dimethylhydantoin as the microbiocide that is mixed with water.

12. The improvement according to any of claims 7, 8, 11 wherein said at least one animal is fowl, swine, sheep, or cattle, and wherein said microbiocidally-effective amount of halogen-based microbiocide in said drinking water is in the range of about 1 to about 100 ppm (wt/wt) expressed as $Br_2$.

13. The improvement according to claim 12 wherein said microbiocidally-effective amount of halogen-based microbiocide in said drinking water is in the range of about 4 to about 30 ppm (wt/wt) expressed as $Br_2$.

14. The improvement according to claim 12 wherein said microbiocidally-effective amount of halogen-based microbiocide in said drinking water is in the range of about 4 to about 50 ppm (wt/wt) expressed as $Br_2$.

15. A method of preparing drinking water for animals to be processed for at least one meat product, the improvement which comprises introducing into said drinking water a microbiocidally-effective amount of at least one 1,3-dibromo-5,5-dialkylhydantoin in the form of solids or as a water solution or slimy formed from said at least one 1,3-dibromo-5,5-dialkylhydantoin, wherein before introduction into any water said at least one 1,3-dibromo-5,5-dialkylhydantoin has a methyl group as one of its alkyl groups and an alkyl group containing in the range of 1 to about 4 carbon atoms as its other alkyl group.

16. The improvement according to claim 15 wherein said microbiocidally-effective amount of halogen-based microbiocide results from use of 1,3-dibromo-5,5-dimethylhydantoin as the microbiocide that is mixed with water.

17. The improvement according to either of claim 15 or 16 wherein said at least one animal is poultry, swine, sheep, or cattle, and wherein said microbiocidally-effective amount of halogen-based microbiocide in said drinking water is in the range of about 1 to about 100 ppm (wt/wt) expressed as $Br_2$.

18. The improvement according to claim 17 wherein said microbiocidally-effective amount is in the range of about 4 to about 30 ppm (wt/wt) expressed as $Br_2$.

19. The improvement according to claim 17 wherein said microbiocidally-effective amount is in the range of about 4 to about 50 ppm (wt/wt) expressed as $Br_2$.

20. A method for reducing fecal contamination in animals to be processed for at least one meat product, which method comprises:

A) preparing drinking water for said animals by introducing into said water a microbiocidally-effective amount of at least one 1,3-dibromo-5,5-dialkylhydantoin in which one of the alkyl groups is a methyl group and the other alkyl group contains in the range of 1 to about 4 carbon atoms to form microbiocidally-treated drinking water; and B) providing microbiocidally-treated drinking water from A) to said animals prior to processing said animals for at least one meat product.

21. A method according to claim 20 wherein said at least 1,3-dibromo-5,5-dialkylhydantoin is 1,3-dibromo-5,5-dimethylhydantoin.

22. A method according to either of claim 20 or 21 wherein said microbiocidally-effective amount is in the range of about 1 to about 100 ppm (wt/wt) expressed as $Br_2$.

23. A method according to claim 22 wherein said microbiocidally-effective amount is in the range of about 4 to about 50 ppm (wt/wt) expressed as $Br_2$.

24. A method according to claim 22 wherein said microbiocidally-effective amount is in the range of about 4 to about 30 ppm (wt/wt) expressed as $Br_2$.

* * * * *

UNITED STATES PATENT AND TRADEMARK OFFICE
CERTIFICATE OF CORRECTION

PATENT NO.       : 6,919,364 B2
APPLICATION NO.  : 10/028631
DATED            : July 19, 2005
INVENTOR(S)      : Jonathan N. Howarth and James L. McNaughton It is certified that error appears in the above-identified patent and that said Letters Patent is hereby corrected as shown below:

On the title page, the statement "This patent is subject to a terminal disclaimer" should be removed from the face of the patent.

On the title page, under References Cited, U.S. Patent Documents, reads "2,888,787 A 1/1959 Paterson" and should read -- 2,868,787 A  1/1959  Paterson --.

On the title page, under References Cited, Foreign Patent Documents, reads "EP 0228583  7/1987" and should read -- EP 0228593  7/1987 --.

On the title page, under References Cited, Foreign Patent Documents, reads "EP 0177845  4/1988". Delete this reference from the face of the Patent.

On the title page, under References Cited, Foreign Patent Documents, reads "EP 0206725  12/1988", and should read -- EP 0206725  12/1986 --.

On page 3, first column Foreign Patent Documents reads "WO 9720548  8/1997", and should read -- WO 9720546  8/1997 --.

On page 3, first column, Foreign Patent Documents, reads "WO 0034188  6/2000", and should read -- WO 0034186  6/2000 --.

On page 4, first column, reads "Scrum — Fundamentals of General Chemistry, p. 315, 1955.", and should read -- Sorum – Fundamentals of General Chemistry, p. 315, 1955. --.

UNITED STATES PATENT AND TRADEMARK OFFICE
CERTIFICATE OF CORRECTION

PATENT NO. : 6,919,364 B2
APPLICATION NO. : 10/028631
DATED : July 19, 2005
INVENTOR(S) : Jonathan N. Howarth and James L. McNaughton It is certified that error appears in the above-identified patent and that said Letters Patent is hereby corrected as shown below:

On page 4, second column, reads "Frosti Abstract of Bocharov D.A., "Disinfection of Poutry Processing Plant Objects", Proceedings of the 22nd European meeting of Meat Research Workers, Malmo, Aug.:Sep., I (C6), 4 pp. ., 1976. Accession No. 78674 Frosti", and should read -- Frosti Abstract of Bocharov D.A., "Disinfection of Poultry Processing Plant Objects", Proceedings of the 22nd European meeting of Meat Research Workers, Malmo, Aug.:Sep., I (C6), 4 pp. 1976. Accession No. 78674 Frosti. --.

On page 4, second column, reads "CAPLUS Abstract of Heir, et al., "The Staphylococcus qacII gene product: a new member of the SMR family encoding multidrug resistance", FEMS Microbiol. Lett. (1998), 163(1), ppg 49-56. Accession No. 1998:343309 CAPLUS", and should read -- CAPLUS Abstract of Heir, et al., "The Staphylococcus qacH gene product: a new member of the SMR family encoding multidrug resistance", FEMS Microbiol. Lett. (1998), 163(1), ppg 49-56. Accession No. 1998:343309 CAPLUS. --.

Claim 15, Column 27, Line 43, reads "solution or slimy", and should read --solution or slurry --.

Signed and Sealed this

Twenty-fifth Day of December, 2007

JON W. DUDAS
*Director of the United States Patent and Trademark Office*